US012766073B2

(12) United States Patent
Schweiss et al.

(10) Patent No.: US 12,766,073 B2
(45) **Date of Patent: *Oct. 20, 2026**

(54) POOLING DEVICE FOR SINGLE OR MULTIPLE MEDICAL CONTAINERS

(71) Applicant: Takeda Pharmaceutical Company Limited, Osaka (JP)

(72) Inventors: Mark David Schweiss, Grayslake, IL (US); Daniel Edward Roush, Niles, IL (US); Stefan Holzner, Vienna (AT); Seth Dale Jones, Round Lake, IL (US); Tejas Dhyani, Mundelein, IL (US); Michelle Shah, South Barrington, IL (US); Madeleine Clare Gibson, Madison, WI (US); Jessica Chung, Northbrook, IL (US); Anthony Martin Looper, Lake Zurich, IL (US)

(73) Assignee: Takeda Pharmaceutical Company Limited, Osaka (JP)

( * ) Notice: Subject to any disclaimer, the term of this patent is extended or adjusted under 35 U.S.C. 154(b) by 590 days.

This patent is subject to a terminal disclaimer.

(21) Appl. No.: 18/316,151

(22) Filed: May 11, 2023

(65) Prior Publication Data

US 2023/0355475 A1 Nov. 9, 2023

Related U.S. Application Data

(63) Continuation of application No. 16/746,583, filed on Jan. 17, 2020, now Pat. No. 11,684,548, which is a
(Continued)

(51) Int. Cl.
*A61J 1/20* (2006.01)
*A61M 5/14* (2006.01)

(52) U.S. Cl.
CPC ........... *A61J 1/2089* (2013.01); *A61J 1/2062* (2015.05); *A61M 5/1407* (2013.01); *A61J 1/201* (2015.05); *A61J 1/2082* (2015.05)

(58) Field of Classification Search
CPC ........ A61J 1/2062; A61J 1/2089; A61J 1/201; A61J 1/2013; A61M 5/1407; A61M 5/16827
See application file for complete search history.

(56) References Cited

U.S. PATENT DOCUMENTS

| | | | |
|---|---|---|---|
| 363,690 | A | 5/1887 | Sleeper |
| 2,080,947 | A | 5/1937 | Ligeour |

(Continued)

FOREIGN PATENT DOCUMENTS

| | | | |
|---|---|---|---|
| CN | 1668352 | A | 9/2005 |
| CN | 1874936 | A | 12/2006 |

(Continued)

OTHER PUBLICATIONS

U.S. Appl. No. 17/282,042, filed Apr. 1, 2021, Jones et al.

(Continued)

*Primary Examiner* — Ariana Zimbouski
(74) *Attorney, Agent, or Firm* — Wolf, Greenfield & Sacks, P.C.

(57) ABSTRACT

A device is provided for pooling a fluid from a container unit having at least one container, and includes an inlet port having at least one inlet channel configured for receiving the fluid or ambient air, and an outlet port having at least one outlet channel configured for delivering the fluid to an attachment. Both inlet and outlet ports are disposed on the device. A cavity is provided for accommodating insertion of the container unit for pooling the fluid from the at least one container. At least one spike is disposed in the cavity and configured for puncturing a stopper of the at least one
(Continued)

container when the container unit transitions from an upper position to a lower position.

20 Claims, 23 Drawing Sheets

Related U.S. Application Data continuation of application No. 15/186,061, filed on Jun. 17, 2016, now Pat. No. 11,219,578.

(60) Provisional application No. 62/182,099, filed on Jun. 19, 2015.

(56) References Cited

U.S. PATENT DOCUMENTS

| | | | |
|---|---|---|---|
| 2,399,893 | A | 5/1946 | Scholz |
| D159,762 | S | 8/1950 | Touhey |
| 2,754,962 | A | 7/1956 | Scrymgeour |
| 2,865,669 | A | 12/1958 | Linthicum |
| 2,949,204 | A | 8/1960 | Edwards |
| 3,278,007 | A | 10/1966 | Weber |
| 3,543,355 | A | 12/1970 | Wyckoff et al. |
| 3,589,509 | A | 6/1971 | Mascia et al. |
| 3,593,873 | A | 7/1971 | Vonk |
| 3,601,253 | A | 8/1971 | Poupitch |
| 3,727,749 | A | 4/1973 | Martin |
| 3,744,661 | A | 7/1973 | Fischer, Jr. |
| 3,876,377 | A | 4/1975 | Cinqualbre |
| 3,882,909 | A | 5/1975 | Ogle |
| 3,893,280 | A | 7/1975 | King |
| 4,143,764 | A | 3/1979 | Moss, III |
| 4,178,152 | A | 12/1979 | Nunogaki |
| 4,262,814 | A | 4/1981 | Roccaforte |
| 4,402,691 | A | 9/1983 | Rosenthal et al. |
| 4,405,315 | A | 9/1983 | Handt |
| 4,526,756 | A | 7/1985 | Wong |
| D280,932 | S | 10/1985 | Green |
| 4,557,727 | A | 12/1985 | Handt |
| D283,640 | S | 4/1986 | Grimes |
| 4,713,064 | A | 12/1987 | Bruno et al. |
| 4,759,756 | A | 7/1988 | Forman et al. |
| 4,795,429 | A | 1/1989 | Feldstein |
| 4,807,777 | A | 2/1989 | Berwald et al. |
| 4,850,972 | A | 7/1989 | Schulman et al. |
| 4,856,647 | A | 8/1989 | Dahne |
| 4,863,049 | A | 9/1989 | Suzuki et al. |
| 4,873,921 | A | 10/1989 | Piane, Sr. |
| D306,645 | S | 3/1990 | Parker |
| 4,915,688 | A | 4/1990 | Bischof et al. |
| 4,915,689 | A | 4/1990 | Theeuwes |
| 4,970,053 | A | 11/1990 | Fechtner |
| 4,978,336 | A | 12/1990 | Capozzi et al. |
| 5,005,721 | A | 4/1991 | Jordan |
| 5,009,309 | A | 4/1991 | Hansen |
| 5,037,390 | A | 8/1991 | Raines et al. |
| 5,040,678 | A | 8/1991 | Lenmark, Sr. et al. |
| 5,061,264 | A | 10/1991 | Scarrow |
| 5,117,997 | A | 6/1992 | Fink |
| 5,148,919 | A | 9/1992 | Rubin |
| 5,290,259 | A | 3/1994 | Fischer |
| 5,304,165 | A | 4/1994 | Haber et al. |
| 5,322,668 | A | 6/1994 | Tomasso |
| D355,260 | S | 2/1995 | Tomasso |
| 5,431,509 | A | 7/1995 | Anderson et al. |
| 5,465,841 | A | 11/1995 | Wilson et al. |
| 5,582,222 | A | 12/1996 | Riall |
| 5,609,248 | A | 3/1997 | Rohrbough et al. |
| 5,725,499 | A | 3/1998 | Silverstein et al. |
| 5,785,701 | A | 7/1998 | Sams et al. |
| 5,810,001 | A | 9/1998 | Genga et al. |
| 5,836,910 | A | 11/1998 | Duffy et al. |
| 5,873,731 | A | 2/1999 | Prendergast |
| 5,897,526 | A | 4/1999 | Vaillancourt |
| 5,941,846 | A | 8/1999 | Duffy et al. |
| 5,954,213 | A | 9/1999 | Gerhart et al. |
| 5,954,313 | A | 9/1999 | Ryan |
| 5,957,313 | A | 9/1999 | Bouan |
| 5,989,237 | A | 11/1999 | Fowles et al. |
| 6,000,548 | A | 12/1999 | Tsals |
| 6,022,339 | A | 2/2000 | Fowles et al. |
| 6,102,232 | A | 8/2000 | Lin et al. |
| 6,102,233 | A | 8/2000 | Waugh |
| 6,164,450 | A | 12/2000 | Benedetti |
| 6,213,529 | B1 | 4/2001 | Kurcz et al. |
| 6,305,541 | B1 | 10/2001 | Tanner et al. |
| D457,949 | S | 5/2002 | Krug et al. |
| 6,474,375 | B2 | 11/2002 | Spero et al. |
| 6,508,791 | B1 | 1/2003 | Guerrero |
| 6,558,628 | B1 | 5/2003 | Reo |
| 6,599,273 | B1 | 7/2003 | Lopez |
| 6,613,283 | B2 | 9/2003 | Reo |
| 6,641,565 | B1 | 11/2003 | Lavi et al. |
| 6,789,828 | B1 | 9/2004 | Borg |
| 6,929,474 | B2 | 8/2005 | Schenck et al. |
| 7,074,205 | B1 | 7/2006 | Duffy et al. |
| 7,214,210 | B2 | 5/2007 | Kamen et al. |
| 7,442,181 | B2 | 10/2008 | Schubert et al. |
| 7,468,049 | B2 | 12/2008 | Laveault |
| 7,553,291 | B2 | 6/2009 | Duffy et al. |
| 7,607,541 | B2 | 10/2009 | Girgis et al. |
| D620,603 | S | 7/2010 | Talmer et al. |
| 7,798,997 | B2 | 9/2010 | Kamen et al. |
| 7,819,342 | B2 | 10/2010 | Spallek et al. |
| D632,802 | S | 2/2011 | Salinas et al. |
| 7,935,076 | B2 | 5/2011 | Estes et al. |
| D645,973 | S | 9/2011 | Hoenes |
| 8,425,487 | B2 | 4/2013 | Beiriger et al. |
| 8,545,440 | B2 | 10/2013 | Patrick et al. |
| 8,652,097 | B2 | 2/2014 | Lee |
| 8,684,433 | B2 | 4/2014 | Oesterle et al. |
| 8,708,950 | B2 | 4/2014 | Scarpaci et al. |
| 8,790,328 | B2 | 7/2014 | Kragelund et al. |
| 8,968,244 | B2 | 3/2015 | Kamen et al. |
| 9,107,809 | B2 | 8/2015 | Garfield et al. |
| 9,132,061 | B2 | 9/2015 | Beiriger |
| D769,456 | S | 10/2016 | Dulaff |
| D778,460 | S | 2/2017 | Marechal et al. |
| 9,597,260 | B2 | 3/2017 | Ivosevic et al. |
| D847,634 | S | 5/2019 | Hatakeyama |
| D847,974 | S | 5/2019 | McNall et al. |
| D865,993 | S | 11/2019 | Trump et al. |
| D886,611 | S | 6/2020 | Jones et al. |
| D890,358 | S | 7/2020 | Jones et al. |
| D893,046 | S | 8/2020 | Jones et al. |
| D902,428 | S | 11/2020 | Klintstedt et al. |
| 11,219,578 | B2 * | 1/2022 | Schweiss .............. A61J 1/2062 |
| 11,684,548 | B2 | 6/2023 | Schweiss et al. |
| 11,903,900 | B2 | 2/2024 | Jones et al. |
| 12,214,161 | B2 | 2/2025 | Jones et al. |
| 12,433,824 | B2 | 10/2025 | Jones et al. |
| 2001/0009994 | A1 | 7/2001 | Small et al. |
| 2002/0004643 | A1 | 1/2002 | Carmel et al. |
| 2002/0104584 | A1 | 8/2002 | Spero et al. |
| 2003/0107628 | A1 | 6/2003 | Fowles et al. |
| 2004/0241041 | A1 | 12/2004 | Woodworth et al. |
| 2004/0260266 | A1 | 12/2004 | Cuschieri et al. |
| 2005/0045495 | A1 | 3/2005 | Dalsing et al. |
| 2005/0126653 | A1 | 6/2005 | Tachikawa et al. |
| 2005/0175338 | A1 | 8/2005 | Ide et al. |
| 2006/0138069 | A1 | 6/2006 | Domkowski et al. |
| 2007/0005020 | A1 | 1/2007 | Laveault |
| 2007/0267378 | A1 | 11/2007 | Piccinino et al. |
| 2007/0278245 | A1 | 12/2007 | Brooks et al. |
| 2009/0062732 | A1 | 3/2009 | Radmer |
| 2009/0099547 | A1 | 4/2009 | Radmer |
| 2009/0182300 | A1 | 7/2009 | Radmer et al. |
| 2010/0022974 | A1 | 1/2010 | Sharratt et al. |
| 2010/0305548 | A1 * | 12/2010 | Kraushaar ............ A61J 1/2096 604/83 |
| 2012/0029464 | A1 | 2/2012 | Kragelund et al. |
| 2012/0053555 | A1 | 3/2012 | Ariagno et al. |
| 2012/0089088 | A1 | 4/2012 | Foshee et al. |

(56) References Cited

U.S. PATENT DOCUMENTS

| | | | |
|---|---|---|---|
| 2012/0127824 A1 | 5/2012 | Petrone | |
| 2012/0298254 A1 | 11/2012 | Brem et al. | |
| 2013/0046270 A1 | 2/2013 | Foshee et al. | |
| 2013/0284735 A1 | 10/2013 | Oesterle et al. | |
| 2014/0021076 A1 | 1/2014 | Soma et al. | |
| 2015/0005734 A1 | 1/2015 | Inoue et al. | |
| 2015/0029816 A1* | 1/2015 | Beyer | B01F 35/7176 366/167.1 |
| 2015/0129589 A1 | 5/2015 | Essler et al. | |
| 2015/0166212 A1 | 6/2015 | Wissner et al. | |
| 2016/0015889 A1 | 1/2016 | Caquias et al. | |
| 2016/0081308 A1 | 3/2016 | Cary et al. | |
| 2016/0266156 A1 | 9/2016 | Brennan et al. | |
| 2017/0020784 A1 | 1/2017 | Schweiss et al. | |
| 2020/0155413 A1 | 5/2020 | Schweiss et al. | |
| 2020/0170884 A1 | 6/2020 | Tashjian | |
| 2021/0172923 A1 | 6/2021 | Kaufman et al. | |
| 2021/0369566 A1 | 12/2021 | Jones et al. | |
| 2021/0369958 A1 | 12/2021 | Jones et al. | |
| 2024/0207138 A1 | 6/2024 | Jones et al. | |
| 2025/0195760 A1 | 6/2025 | Jones et al. | |

FOREIGN PATENT DOCUMENTS

| | | |
|---|---|---|
| CN | 101370534 A | 2/2009 |
| CN | 102387827 A | 3/2012 |
| CN | 202184989 U | 4/2012 |
| CN | 2022036710 U | 5/2012 |
| CN | 102711710 A | 10/2012 |
| CN | 102958455 A | 3/2013 |
| CN | 103402481 A | 11/2013 |
| CN | 103990201 A | 8/2014 |
| CN | 104363877 A | 2/2015 |
| CN | 106413661 A | 2/2017 |
| CN | 206045076 U | 3/2017 |
| CN | 206120865 U | 4/2017 |
| CN | 108040465 A | 5/2018 |
| CN | 108093623 A | 5/2018 |
| CN | 207591040 U | 7/2018 |
| CN | 108366904 A | 8/2018 |
| CN | 108602591 A | 9/2018 |
| CN | 201830503853.6 | 9/2018 |
| CO | 7061051 A2 | 9/2014 |
| CO | 14277741 | 12/2014 |
| DE | 202009012540 U1 | 10/2010 |
| EP | 0 495 808 B1 | 7/1992 |
| EP | 0 631 816 A1 | 1/1995 |
| EP | 0 734 963 B1 | 10/1996 |
| EP | 1 181 921 A2 | 2/2002 |
| EP | 3 569 216 A1 | 11/2019 |
| FR | 2 085 307 A1 | 12/1971 |
| FR | 2 715 131 A1 | 7/1995 |
| JP | S63-68166 A | 3/1988 |
| JP | H07-52954 A | 2/1995 |
| JP | 08-324571 A | 12/1996 |
| JP | 2002-011097 A | 1/2002 |
| JP | 3142209 U | 6/2008 |
| JP | 2009-153720 A | 7/2009 |
| JP | 2011-004805 A | 1/2011 |
| JP | 2012-528692 A | 11/2012 |
| JP | D1463610 | 3/2013 |
| JP | 2013-515925 A | 5/2013 |
| JP | 2013-536049 A | 9/2013 |
| JP | 2014-504921 A | 2/2014 |
| JP | 2015-501688 A | 1/2015 |
| JP | 2015-503964 A | 2/2015 |
| JP | 2015-509421 A | 3/2015 |
| JP | D2016-11117 | 5/2016 |
| JP | 2016-524513 A | 8/2016 |
| JP | 2018-519141 A | 7/2018 |
| RU | 2136326 C1 | 9/1999 |
| RU | 2554852 C2 | 6/2015 |
| TW | 455382 | 9/2001 |
| TW | 201707670 A | 3/2017 |
| TW | D194378 | 12/2018 |
| WO | WO 1990/11103 A2 | 10/1990 |
| WO | WO 93/01739 A1 | 2/1993 |
| WO | WO 94/27669 A1 | 12/1994 |
| WO | WO 1996/032917 A1 | 10/1996 |
| WO | WO 99/27886 A1 | 6/1999 |
| WO | WO 03/054552 A2 | 7/2003 |
| WO | WO 2004/032808 A2 | 4/2004 |
| WO | WO 2009/083347 A1 | 7/2009 |
| WO | WO 2010/043683 A1 | 4/2010 |
| WO | WO 2010/058806 A1 | 5/2010 |
| WO | WO 2010/141632 A2 | 12/2010 |
| WO | WO 2011/079225 A1 | 6/2011 |
| WO | WO 2012/102216 | 8/2012 |
| WO | WO 2013/126055 A1 | 8/2013 |
| WO | WO 2013/162959 A1 | 10/2013 |
| WO | WO 2014/204894 A2 | 12/2014 |
| WO | WO 2015/006822 A1 | 1/2015 |
| WO | WO 2016/011450 A1 | 1/2016 |
| WO | WO 2016/152016 A1 | 9/2016 |
| WO | WO 2016/205687 A1 | 12/2016 |

OTHER PUBLICATIONS

U.S. Appl. No. 17/282,132, filed Apr. 1, 2021, Jones et al.

PCT/US2013/368769, Jul. 26, 2013, International Search Report and Written Opinion.

PCT/US2013/368769, Nov. 6, 2014, International Preliminary Report on Patentability.

CN 201680035766.0, Jan. 16, 2020, Chinese Office Action with English Translation.

NC 2017/0012908, Jul. 26, 2019, Columbian Office Action and English Summary.

EP 19169568.3, Aug. 6, 2019, Extended European Search Report.

PCT/US2016/038136, Dec. 28, 2017, International Preliminary Report on Patentability.

PCT/US2016/038136, Aug. 17, 2016, International Search Report and Written Opinion.

PCT/US2019/052572, Feb. 26, 2020, Invitation to Pay Additional Fees.

PCT/US2019/052572, Jun. 24, 2020, International Search Report and Written Opinion.

PCT/US2019/052572, Apr. 15, 2021, International Preliminary Report on Patentability.

PCT/US2019/052574, Jan. 9, 2020, Invitation to Pay Additional Fees.

PCT/US2019/052574, Mar. 2, 2020, International Search Report and Written Opinion.

PCT/US2019/052574, Apr. 15, 2021, International Preliminary Report on Patentability.

U.S. Appl. No. 18/403,533, filed Jan. 3, 2024, Jones et al.

Chinese Office Action issued Jan. 16, 2020 with English translation in connection with Chinese Application No. 201680035766.0.

Columbian Office Action dated Jul. 26, 2019 and English summary thereof in connection with Columbian Application No. NC2017/0012908.

Extended European Search Report dated Aug. 6, 2019 in connection with European Application No. 19169568.3.

International Search Report and Written Opinion mailed Jul. 26, 2013 in connection with International Application No. PCT/US2013/0368769.

International Preliminary Report on Patentability mailed Nov. 6, 2014 in connection with International Application No. PCT/US2013/036879.

International Search Report and Written Opinion mailed Aug. 17, 2016 in connection with International Application No. PCT/US2016/038136.

International Preliminary Report on Patentability mailed Dec. 28, 2017 in connection with International Application No. PCT/US2016/038136.

Invitation to Pay Additional Fees mailed Jan. 9, 2020 in connection with International Application No. PCT/US2019/052574.

Invitation to Pay Additional Fees mailed Feb. 26, 2020 in connection with International Application No. PCT/US2019/052572.

(56) References Cited

OTHER PUBLICATIONS

International Search Report and Written Opinion mailed Mar. 2, 2020 in connection with International Application No. PCT/US2019/052574.
International Search Report and Written Opinion mailed Jun. 24, 2020 in connection with International Application No. PCT/US2019/052572.
International Preliminary Report on Patentability mailed Apr. 15, 2021 in connection with International Application No. PCT/US2019/052572.
International Preliminary Report on Patentability mailed Apr. 15, 2021 in connection with International Application No. PCT/US2019/052574.
Tractor S.C. Online. Published date unknown. Retrieved on Jan. 9, 2020 from URL: https://en.wikipedia.org/wiki/Tractor_S.C.

* cited by examiner

POOLING DEVICE FOR SINGLE OR MULTIPLE MEDICAL CONTAINERS

CROSS-REFERENCE

The present application is a continuation of U.S. application Ser. No. 16/746,583, filed Jan. 17, 2020, which is a continuation of U.S. application Ser. No. 15/186,061, filed Jun. 17, 2016, which claims the benefit of U.S. Provisional Application No. 62/182,099, filed Jun. 19, 2015. The contents of these applications are incorporated herein by reference in their entirety.

BACKGROUND

The present disclosure generally relates to pooling devices used for medical purposes, and more specifically to a device configured for pooling contents from medicinal containers for concurrent use.

In many cases, medicinal agents or fluids are separated before use for their chemical and physical stability. Thus, the fluids are packaged and stored individually until the fluids are mixed together to be administered intravenously to a patient. Traditionally, the mixing of the fluids is achieved by a medical professional by injecting a first fluid into a glass vial or container having a second fluid. After mixing the first and second fluids, a mixed solution is withdrawn into a syringe barrel and intravenously injected into the patient. In certain cases, the two solutions are mixed in, or mixed solution is transferred to, a larger container, such as an intravenous (IV) administration bag or set, before delivery to the patient.

Some medicinal fluids are administered in sequence without mixing. For example, the first fluid may be administered initially to improve the conditions under which the second fluid is delivered to or processed by the patient. An exemplary dual medical container unit for administering the first and second fluids is described in commonly assigned U.S. Pat. No. 8,684,433, which is incorporated by reference. In some cases, several vials of medicinal fluid must be combined to provide the correct dose to a patient. Patients suffering from certain immunodeficiency conditions are treated with infusions of relatively large volumes of Immunoglobulin (IG) fluid. A first fluid medication is applied to enhance the bodily reception to the relatively high viscosity IG fluid, which is the second medication. Conventionally, the medical professional administering the fluids verifies the identity and concentration of the fluids, swabs a corresponding stopper of each container using a disinfecting agent, such as alcohol, spikes the stopper of each container for the delivery of fluids, pools the fluids separately from respective containers using multiple syringes and pooling bags, and then sequentially performs the administration of the fluids on the patient. In certain cases, the dual container unit is manually elevated or hung from an IV pole so that one or more of the fluids are delivered by gravity flow to the pooling bag.

Due to this multi-step process, which in some cases is alternately performed by the patient at home, the conventional administration method is prone to mishandling and mistakes. For example, the bottles, vials or other containers may be mishandled, and could even end up damaged or broken. Further, several manual steps are currently needed to achieve the desired sequence of administration in a sterile environment, a significant amount of time is wasted due to the numerous manual steps, and a substantial space is required for storing an inventory of equipment during use. If the sterile administration of the medicinal fluid could be compromised, bacterial or environmental contamination could result. Any of these issues may have a negative impact on the administration of the fluids to the patient, and on the health of the patient.

Thus, there is a need for developing an improved pooling device that provides an enhanced administration method for single or multiple medicinal containers in a simpler and more reliable manner.

SUMMARY

The present disclosure is directed to a pooling device for pooling a medicinal fluid from at least one medical container, which integrates many of the manual steps discussed above. An important aspect of the present pooling device is that a central cavity configured for receiving the medical container is provided for pooling the medicinal fluid from the medical container without repeatedly loading different medical containers. An internal lumen spike is disposed in the cavity for puncturing a stopper of each medical container, and a locking mechanism is provided for securely holding the medical container in the cavity of the present pooling device.

In some embodiments, two or more present pooling devices are linkable or connectable in a complementary relationship, such that separate medical containers are sequentially automatically administered to a user or patient without having to replace the medical container during operation. As an example only, an outlet of the present pooling device is linked or daisy-chained to an inlet of another pooling device for facilitating an unbroken connection of the fluid path between all linked pooling devices. In this configuration, two or more medicinal fluids can be administered to the user in relatively high volumes (in the range of 100's of ml) without interruption or manipulation of the medical containers. It is contemplated that the linked pooling devices can be reversed from the orientation described above.

In one embodiment, a pooling device is provided for pooling a fluid from a container unit having at least one container, and includes an inlet port having at least one inlet channel configured for receiving the fluid or ambient air, and an outlet port having at least one outlet channel configured for delivering the fluid to an attachment. Both inlet and outlet ports are disposed on the device. A cavity is provided for accommodating insertion of the container unit for pooling the fluid from the at least one container. At least one spike is disposed in the cavity and configured for puncturing a stopper of the at least one container when the container unit transitions from an upper position to a lower position.

In another embodiment, a pooling device is provided for pooling a medicinal fluid, and includes a container unit having at least one container configured for storing the fluid, wherein the container unit is pre-attached to the pooling device. Also included in the pooling device is an inlet port having at least one inlet channel configured for receiving the fluid or ambient air. An outlet port having at least one outlet channel is provided for delivering the fluid to an attachment. Both inlet and outlet ports are disposed on the pooling device. A cavity is provided for accommodating insertion of the container unit from the pre-attached position for pooling the fluid from the at least one container. At least one spike is disposed in the cavity and configured for puncturing a stopper of the at least one container when the container unit transitions from an upper position to a lower position.

In yet another embodiment, a device is provided for pooling a medicinal fluid, and includes a container unit having at least one container configured for storing the fluid, wherein the container unit is pre-attached to the pooling device. An inlet port having at least one inlet channel is provided for receiving the fluid or ambient air. An outlet port having at least one outlet channel is provided for delivering the fluid to an attachment. Both inlet and outlet ports are disposed on the pooling device. A cavity is provided for accommodating insertion of the container unit from the pre-attached position for pooling the fluid from the at least one container. At least one spike is disposed in the cavity and configured for puncturing a stopper of the at least one container when the container unit transitions from an upper position to a lower position. The pooling device is complementarily linkable with another pooling device in a serial arrangement relative to a longitudinal axis of each pooling device for establishing an uninterrupted supply of the fluid from linked pooling devices.

In yet another embodiment, a pooling device is provided for pooling a fluid from a container unit having at least one container, and includes an inlet port having at least one inlet channel configured for receiving the fluid or ambient air. Also included in the pooling device is an outlet port having at least one outlet channel configured for delivering the fluid to an attachment, and the inlet and outlet ports are disposed on the pooling device. A cavity is configured for accommodating insertion of the container unit for pooling the fluid from the at least one container. At least one spike is disposed in the cavity and configured for puncturing a stopper of the at least one container when the container unit transitions from an upper position to a lower position.

More specifically, the inlet port is connected to the outlet port in fluid communication with the at least one spike via a corresponding tube, and the at least one spike has a first spike channel being connected to the at least one inlet channel. Further, the at least one spike has a second spike channel being connected to the at least one outlet channel. At least one of the inlet and outlet ports has a protective cover for guarding the corresponding inlet and outlet channels from contamination, and the at least one spike projects normally from an inner surface of a base of the pooling device.

A locking mechanism is provided for the pooling device and is configured for securely holding the container unit in the cavity during use, and the locking mechanism is preferably disposed on an inner wall of the cavity. The cavity is configured for accommodating insertion of the container unit for pooling the fluid from a single container. At least one container is configured to store the fluid, and the container unit is attached to the pooling device. A lockout mechanism is provided for the pooling device, and is configured for stopping the transition of the container unit from the upper position to the lower position.

For the container unit, a lockout pin is included and is insertable into a slot disposed on a body of the container unit. A press bar is disposed on a top of the container unit for transitioning the container unit from the upper position to the lower position by pushing the press bar downwardly. Advantageously, the pooling device is serially linkable with another pooling device in a complementary relationship for establishing an uninterrupted supply of the fluid from linked pooling devices. Preferably, the inlet port of a first pooling device is configured to be insertable into the outlet port of a second pooling device in a complementary relationship. A first pooling device and a second pooling device are serially linked together in a complementary relationship relative to a longitudinal axis of each pooling device.

A cap remover is provided for the pooling device, and is attached to the at least one container and configured for removing a top cap of the at least one container. A leakage prevention mechanism has a fluid connection assembly configured for controlling a fluid path in the pooling device, and an air connection assembly configured for controlling an air vent path in the pooling device. The air connection assembly includes an air path connector being connected to the inlet port of the pooling device via a hydrophobic filter.

Included in the fluid connection assembly is a first fluid check valve being connected to the outlet port of the pooling device for selectively regulating a directional fluid flow of the fluid, and a second fluid check valve being connected to the inlet port of the pooling device for selectively regulating the directional fluid flow of the fluid. The first fluid check valve has a first fluid path connector configured for releasably complementarily connecting to a second check valve of another pooling device, and the second fluid check valve has a second fluid path connector configured for releasably complementarily connecting to the first fluid check valve of another pooling device. A cracking pressure of the first and second fluid check valves is in a range of 3-5 pounds per square inch.

Included in the air connection assembly is an air path plug or end component member having a blind cavity configured for releasably complementarily connecting to the air path connector of another pooling device. The fluid connection assembly includes a first female member having a first female member opening configured for accommodating insertion of a first male member of the fluid connection assembly. Also, the fluid connection assembly includes an assembly locking mechanism configured for releasably connecting the first female and male members of the fluid connection assembly. Specifically, the first female member has a first sealing fixture configured for preventing a directional fluid flow of the fluid, and the first male member has a second sealing fixture configured for preventing the directional fluid flow of the fluid. Further, the first female member has a column depending from an inner upper surface of the first female member, and the first male member has a backup washer having a central throughbore dimensioned to accommodate insertion of the column of the first female member. Also included in the air connection assembly is a second female member having a second female member opening configured for accommodating insertion of a second male member of the air connection assembly.

A hydrophobic filter is disposed in the second female member opening of the second female member, and the second male member is configured for creating an air-tight interference-fit between the sheath and the second female member. Preferably, the second male member is enclosed with a sheath having an annular protrusion. A plurality of fluid and air path tubes are provided in the pooling device, and the path tubes are constructed and arranged for placing at least one of the air vent path and the fluid path of the pooling device in fluid communication with each other.

It is preferred that the air connection assembly is simultaneously connected to and shared by at least two containers of the pooling device, and the fluid connection assembly includes a first force-activated valve being connected to the outlet port of the pooling device for selectively regulating a directional fluid flow of the fluid. Also, the fluid connection assembly includes a second force-activated valve being connected to the inlet port of the pooling device for selectively regulating the directional fluid flow of the fluid.

Included in the fluid connection assembly is a unidirectional check valve being connected to the inlet port of the pooling device for selectively regulating a directional fluid flow of the fluid.

At least one spike is enclosed with a spike sheath configured for connecting the inlet and outlet ports of the pooling device in fluid communication. The fluid connection assembly includes a spike connector and an access dome valve. Specifically, the access dome valve has an opening configured for accommodating insertion of the spike connector in a complementary relationship. The fluid connection assembly includes at least one of: a hydrophobic filter and a hydrophilic filter. It is preferred that the hydrophobic filter is connected to the inlet port of the pooling device for selectively regulating a directional air flow of the pooling device. Alternatively or additionally, the hydrophilic filter is connected to the outlet port of the pooling device for selectively regulating a directional fluid flow of the pooling device.

A tray member includes at least one pooling device which is incorporated into the tray member in fluid communication. Preferably, the tray member includes a flow cover having at least one flow passageway and being attached to the tray member for facilitating the fluid communication. Further, the tray member includes a positional valve configured for selectively regulating a flow path from at least one container. At least one hydrophobic filter is connected to at least one of: the inlet port and the outlet port. Similarly, at least one hydrophilic filter is connected to at least one of: the inlet port and the outlet port. In another embodiment, a tray member includes a plurality of pooling devices incorporated into the tray member in fluid communication. In this configuration, it is preferred that the tray member includes two separate tubes configured for conveying two separate fluids from the plurality of pooling devices to the outlet port.

In yet another embodiment, a pooling device is provided for pooling a medicinal fluid, and includes a container unit having at least one container configured to store the fluid, the container unit being attached to the pooling device. An inlet port has at least one inlet channel configured for receiving the fluid or ambient air. An outlet port has at least one outlet channel configured for delivering the fluid to an attachment, where the inlet and outlet ports are disposed on the pooling device. A cavity is configured for accommodating insertion of the container unit for pooling the fluid from the at least one container. At least one spike is disposed in the cavity and configured for puncturing a stopper of the at least one container when the container unit transitions from an upper position to a lower position. The pooling device is complementarily linkable with another pooling device in a serial arrangement relative to each pooling device for establishing an uninterrupted supply of the fluid from linked pooling devices. Also included in the pooling device is a first wing configured for accommodating the outlet port, and a second wing configured for accommodating the inlet port. The second wing is vertically displaced relative to the first wing.

The foregoing and other aspects and features of the disclosure will become apparent to those of reasonable skill in the art from the following detailed description, as considered in conjunction with the accompanying drawings.

DETAILED DESCRIPTION

Although a particular embodiment of the present pooling device has been described herein, other alternate embodiments of all components related to the present pooling device are interchangeable to suit different applications. The term "pooling device" as used in this application refers to a device for accessing the medicinal fluid from one or more medical containers for administering the medicinal fluid to a patient. Thus, a pooling device used to administer medicinal fluid from a single container is contemplated, as well as several medical containers.

Figure 1:
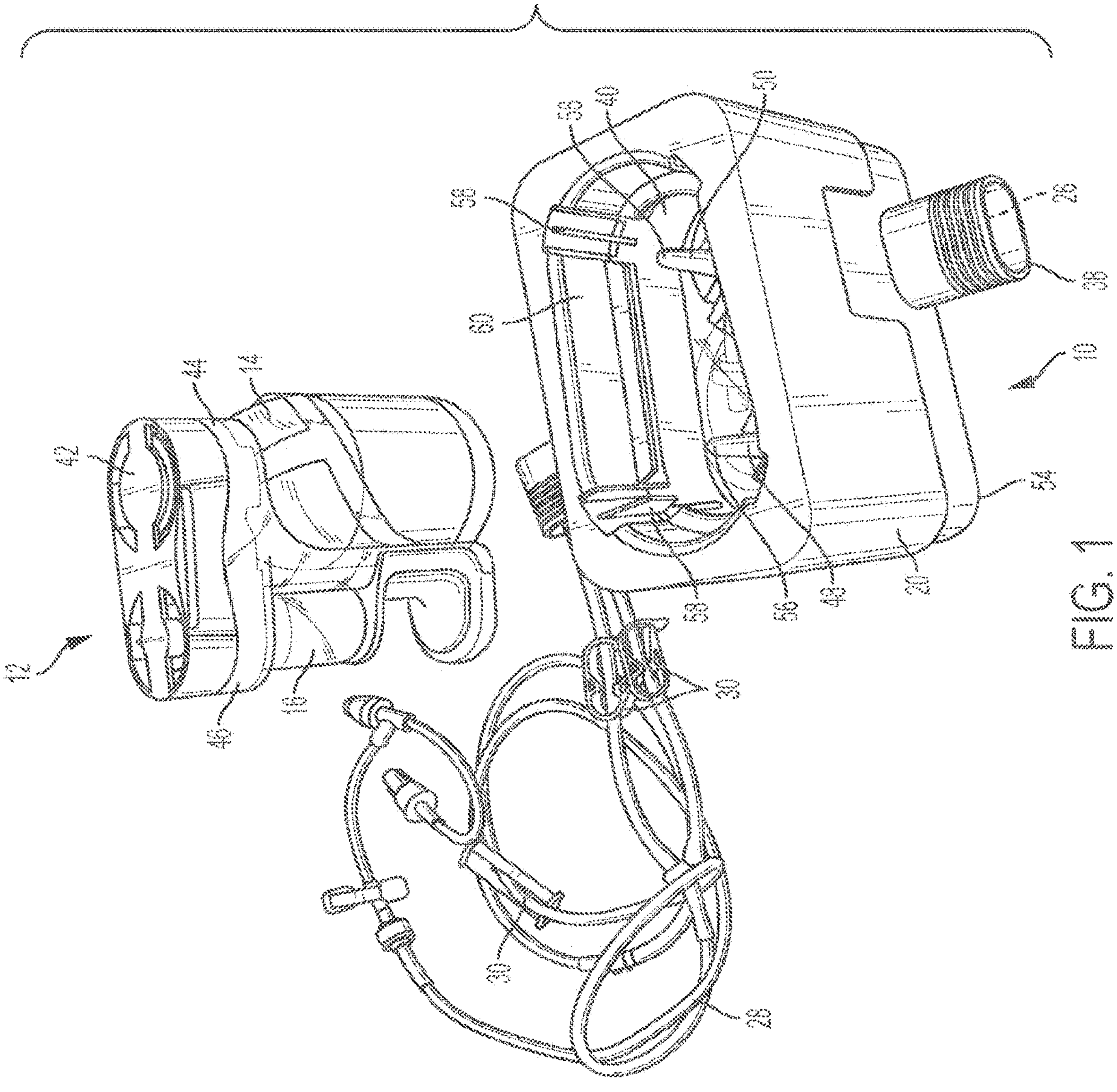
FIG. 1 is a perspective view of a first embodiment of the present pooling device, featuring an exemplary dual medical container unit and an exemplary infusion tubing set.
Figure 2:
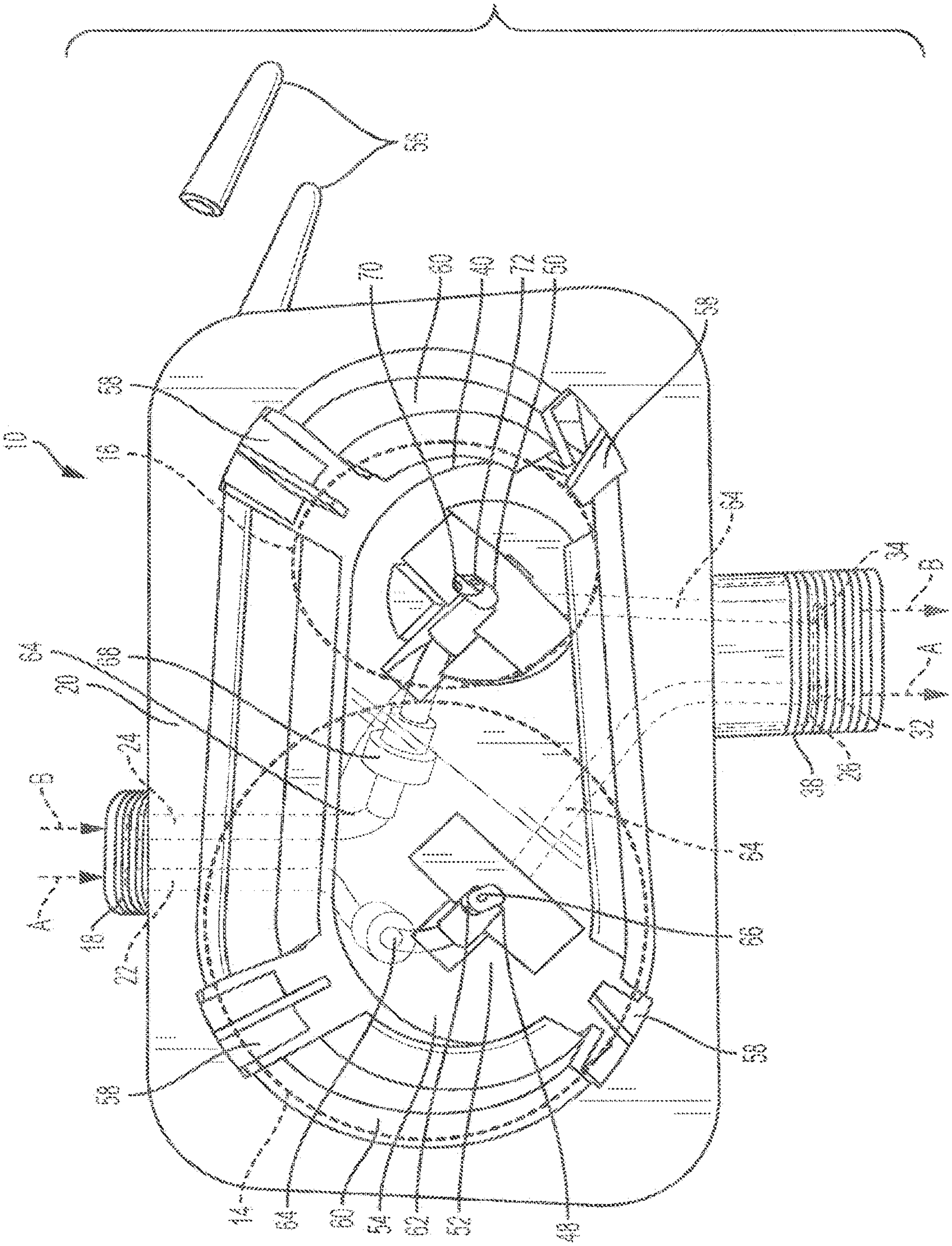
FIG. 2 is a plan view of the pooling device of FIG. 1, featuring exemplary inlet and outlet ports for fluid delivery, and integrated spikes transversely disposed on an inner surface of the pooling device for puncturing stoppers of corresponding medical containers.
Figure 3:
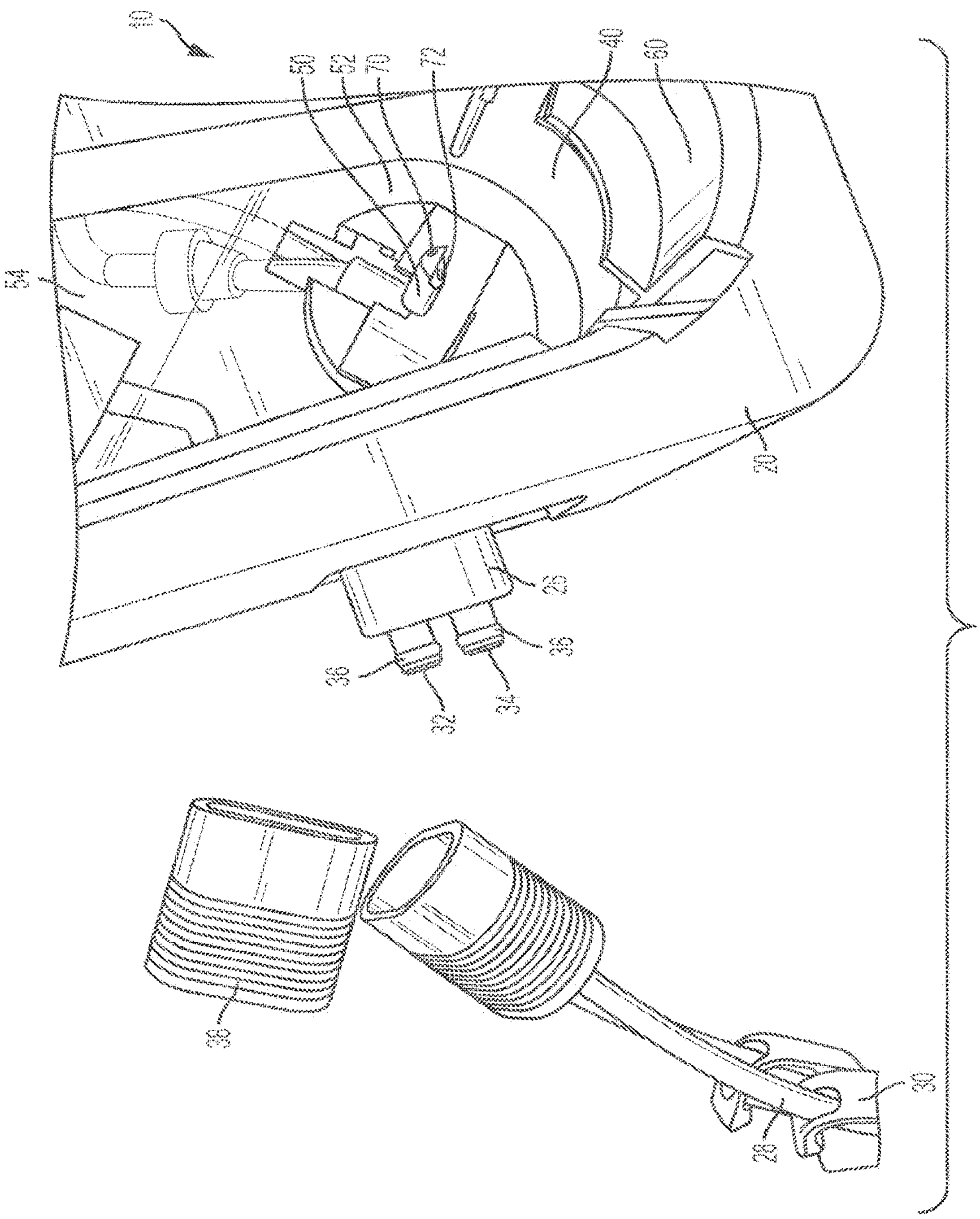
FIG. 3 is a partial plan view of the pooling device of FIG. 2, featuring the exemplary outlet port disposed on an outer surface of the pooling device for detachably connecting to the infusion tubing set.

Referring now to FIGS. 1-3, the present pooling device is generally designated 10 and is designed to pool a medicinal fluid or substance from a medical container unit, generally designated 12, having a first medical container 14 configured for storing a first medicinal fluid, and a second medical container 16 configured for storing a second medicinal fluid. In some embodiments, the present pooling device 10 is a disposable unit, to avoid potential contamination from re-use. As discussed above, an exemplary dual medical container unit 12 is described in commonly assigned U.S. Pat. No. 8,684,433, which is incorporated by reference. While other medicinal substances are contemplated for use with the present device 10, in one embodiment, the first medical container 16 contains an enzyme that enlarges pores in the subcutaneous space of the patient. Enlargement of the pores facilitate the delivery by infusion of high volumes of relatively high viscosity IG fluid, which is contained in the second container 14. For example, without the enzyme, an expected infusion of IG fluid is approximately 50 ml at a single site. However, with the enzyme, infusions in the range of 600 ml can be achieved at a single infusion site.

While the container unit 12 having two medical containers 14, 16 is shown, it is also contemplated that the container unit has a single container (e.g., a syringe, vial, film bag, ampule, and the like). In one embodiment, the present pooling device 10 has a substantially rectangular shape when viewed from above, but other suitable shapes, such as oval, square, and other geometric shapes, are contemplated. It is also contemplated that any number or combination of medical containers can be used for the present pooling device 10 to suit different applications.

Included in the present pooling device 10 is an inlet port 18 configured for receiving the medicinal fluid or ambient air, and the inlet port is disposed on an outer wall 20 of the pooling device. In some embodiments, as described in greater detail below, the inlet port 18 receives the medicinal fluid from an adjacent pooling device (FIGS. 4 and 5) when the pooling devices are linked together. Otherwise, the inlet port 18 acts as a vent for drawing ambient air while the pooling device 10 is not linked to the adjacent pooling device. As described below in relation to FIG. 6, when the pooling devices 10 are linked together, the proper venting of air between the respective devices and containers has been found to enhance the sequential delivery of the medications. Depending on the configuration of the container unit 12, the inlet port 18 may have one or more inlet channels 22, 24 that correspond to the medical containers 14, 16 during use.

For delivering the medicinal fluid from the pooling device 10, an outlet port 26 is disposed on an opposite side of the outer wall 20 of the pooling device from the inlet port 18, and is configured for delivering the medicinal fluid to another medical attachment, such as the adjacent pooling device or an infusion tubing set 28. In some embodiments, the infusion tubing set 28 is detachably connected at one end to the outlet port 26 of the pooling device 10, and at an opposite end to a pumping system (not shown), such as a peristaltic pump or an infusion device, for drawing the medicinal fluid from the pooling device 10. Alternatively, a syringe (not shown) can be docked to the outlet port 26 for vacuum withdrawal of the medicinal fluid from the pooling device 10.

Regulating a flow of the medicinal fluid in the tubing set 28 is achieved by transversely adjusting at least one clamp 30 relative to a longitudinal axis of corresponding tubing. Other clamping devices that transition between an occluding position and a non-occluding position are contemplated as known in the art. As is the case with the inlet port 18, the outlet port 26 may have one or more outlet channels 32, 34 that correspond to the medical containers 14, 16 during use.

In some embodiments, each channel 22, 24, 32, 34 has a resiliently deformable seal 36, such as an O-ring or the like, located at an entrance of the corresponding channel for facilitating a friction fit or slip-connection between connected inlet and outlet ports 18, 26, or between the outlet port 26 and the infusion tubing set 28. It is contemplated that a removable protective cover 38 is friction fit over or around each port 18, 26 to guard the corresponding inlet and outlet channels 22, 24, 32, 34 from touch or air contamination.

In some embodiments, a central opening or cavity 40 configured for accommodating insertion of the medical container unit 12 is provided for pooling the first and second medicinal fluids from the first and second medical containers 14, 16. Before the insertion of the medical container unit 12 into the cavity 40, a top cap 42 of the medical container unit is removed to expose first and second stoppers 44, 46 of the corresponding first and second containers 14, 16. Terminal sterilization of the stoppers 44, 46 is performed using a disinfecting agent, such as alcohol, hydrogen peroxide, or the like.

A first lumen spike or needle 48 is disposed in the cavity 40 for puncturing the first stopper 44 of the first medical container 14, and a second lumen spike or needle 50 is disposed in the cavity for puncturing the second stopper 46 of the second medical container 16. Both spikes 48, 50 are preferably integrally transversely attached to an inner surface 52 of a base 54 of the pooling device 10, such that the spikes project normally from the base for simultaneously puncturing the first and second stoppers 44, 46 of the corresponding first and second medical containers 14, 16. In certain cases, the first and second stoppers 44, 46 of the corresponding first and second containers 14, 16 are punctured separately to suit different applications. In some embodiments, a protective removable sleeve or sheath 56 is provided for each spike 48, 50 to cover a sharp end point of each spike.

Initiation of medicinal fluid delivery is achieved by inverting the container unit 12 and inserting the container unit into the cavity 40, such that the container unit transitions from an upper position to a lower position. Specifically, in this depicted embodiment, during the insertion, the first and second stoppers 44, 46 of the first and second containers 14, 16 are pressed against and punctured by the first and second lumen spikes 48, 50, respectively. It is also contemplated that the protective seal provided by sleeve 56 is breached upon the inversion and downward insertion of the container unit 12. A biased, clip or clamp-type locking mechanism 58, disposed on an inner wall 60 of the cavity 40 in this depicted embodiment, is provided for holding the container unit 12 spaced above the base 54 so that the containers 14, 16 are unable to reach the spikes 48, 50 unless the containers are correctly located over the appropriate spike.

To facilitate proper orientation of the containers in the unit 12, as seen in FIG. 2, the cavity 40 is dimensioned so that the container unit 12 is keyed to the cavity so that it can only be inserted in the correct orientation. Once the containers 14, 16 are properly positioned in the cavity 40, the locking clips 58 are pushed radially outwardly by the presence of the containers, which permits the container unit 12 to telescope, slide or move downwardly relative to the base 54, enabling engagement between the containers and the designated spike 48, 50. The spikes 48, 50 pierce the stoppers 44, 46 of the corresponding containers 14, 16 and initiates the delivery of the respective contained medicinal fluids.

To facilitate the fluid delivery of the first medicinal fluid, the first spike 48 has a first spike channel 62 being connected, via corresponding tubing 64, to the first inlet channel 22. Further, the first spike 48 has a second spike channel 66 being connected, via the corresponding tubing 64, to the first outlet channel 32. In a preferred embodiment, at least one check valve 68 is interposed or installed in the tubing 64 to selectively control a directional flow of the medicinal fluid. It is contemplated that the term "tube" or "tubing" includes or relates to any fixed or flexible fluid passageways or paths, such as grooves and the like, either separate from, or integral with the present pooling device 10, having a variety of cross-sectional shapes (e.g., rounded, squared, or other shapes) depending on the application and construction methods.

It is contemplated that the tubing 64 is configured to interconnect the inlet port 18, the spikes 48, 50, and the outlet port 26, as known in the art. As a result, upon activation of the pooling device 10, a continuous flow path is established from the inlet port 18 to the outlet port 26 in fluid communication with the first container 14. As described in greater detail below in paragraphs related to FIGS. 10-16, it is also contemplated that a hydrophobic filter is used in the tubing 64 or other suitable locations of the pooling device 10 to allow air to pass through, but prevent the medicinal fluid from leaking out of the pooling device. Additional check valves may be installed under the base 54 to prevent the medicinal fluid from traveling to a connected adjacent unit via the spikes 48, 50.

More specifically, as illustrated in FIG. 2, in a configuration where the present pooling device 10 is not linked to another pooling device, ambient air is drawn into the first container 14 (shown in phantom in FIG. 2) under the action of the pumping system via the first inlet channel 22, the corresponding tubing 64, and the first spike channel 62 of the first spike 48. As a result, the first medicinal fluid in the first container 14 is delivered to the first outlet channel 32 via the second spike channel 66 of the first spike 48 and the corresponding tubing 64. An exemplary flow path of the air and the first medicinal fluid is designated with a broken-line arrow A.

When the delivery of the first medicinal fluid is completed, the delivery of the second medicinal fluid may be initiated by controlling opening and closing of the clamps 30 (FIG. 3). To facilitate the fluid delivery of the second medicinal fluid, the second spike 50 has a first spike channel 70 being connected, via the corresponding tubing 64, to the second inlet channel 24. Further, the second spike 50 has a second spike channel 72 being connected, via the corresponding tubing 64, to the second outlet channel 34. Consequently, upon activation of the pooling device 10, another continuous flow path is established from the inlet port 18 to the outlet port 26 in fluid communication with the second container 16 (shown in phantom in FIG. 2).

Specifically, as is the case with the first spike 48, ambient air is drawn into the second container 16 under the action of the pumping system via the second inlet channel 24, the corresponding tubing 64, and the first spike channel 70 of the second spike 50. As a result, the second medicinal fluid in the second container 16 is delivered to the second outlet channel 34 via the second spike channel 72 of the second spike 50 and the corresponding tubing 64. An exemplary flow path of the air and the second medicinal fluid is designated with a broken-line arrow B.

Figure 4:
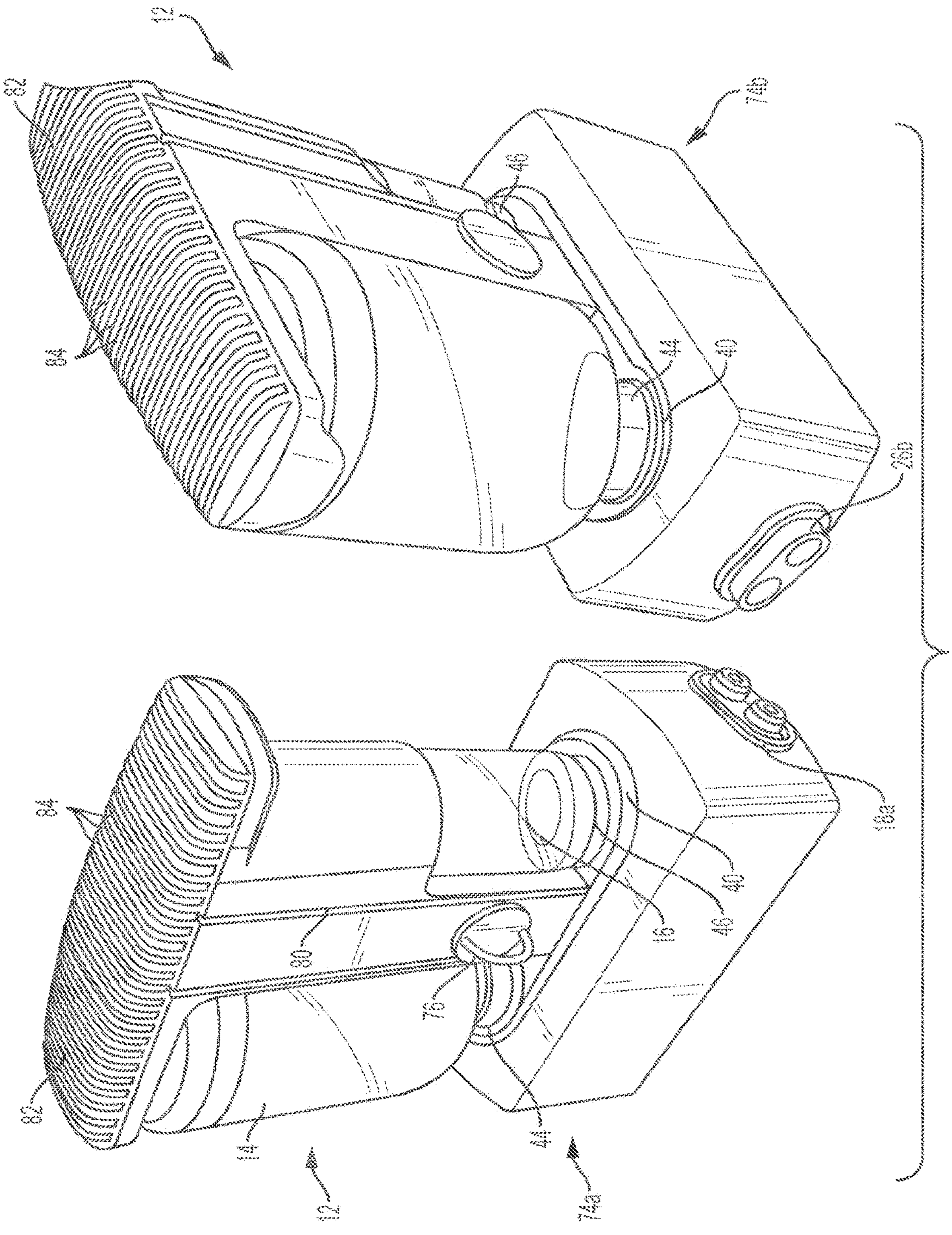
FIG. 4 is a perspective view of a second embodiment of the present pooling device having a lockout pin, illustrating an exemplary arrangement of two adjacent pooling devices before connection.
Figure 5:
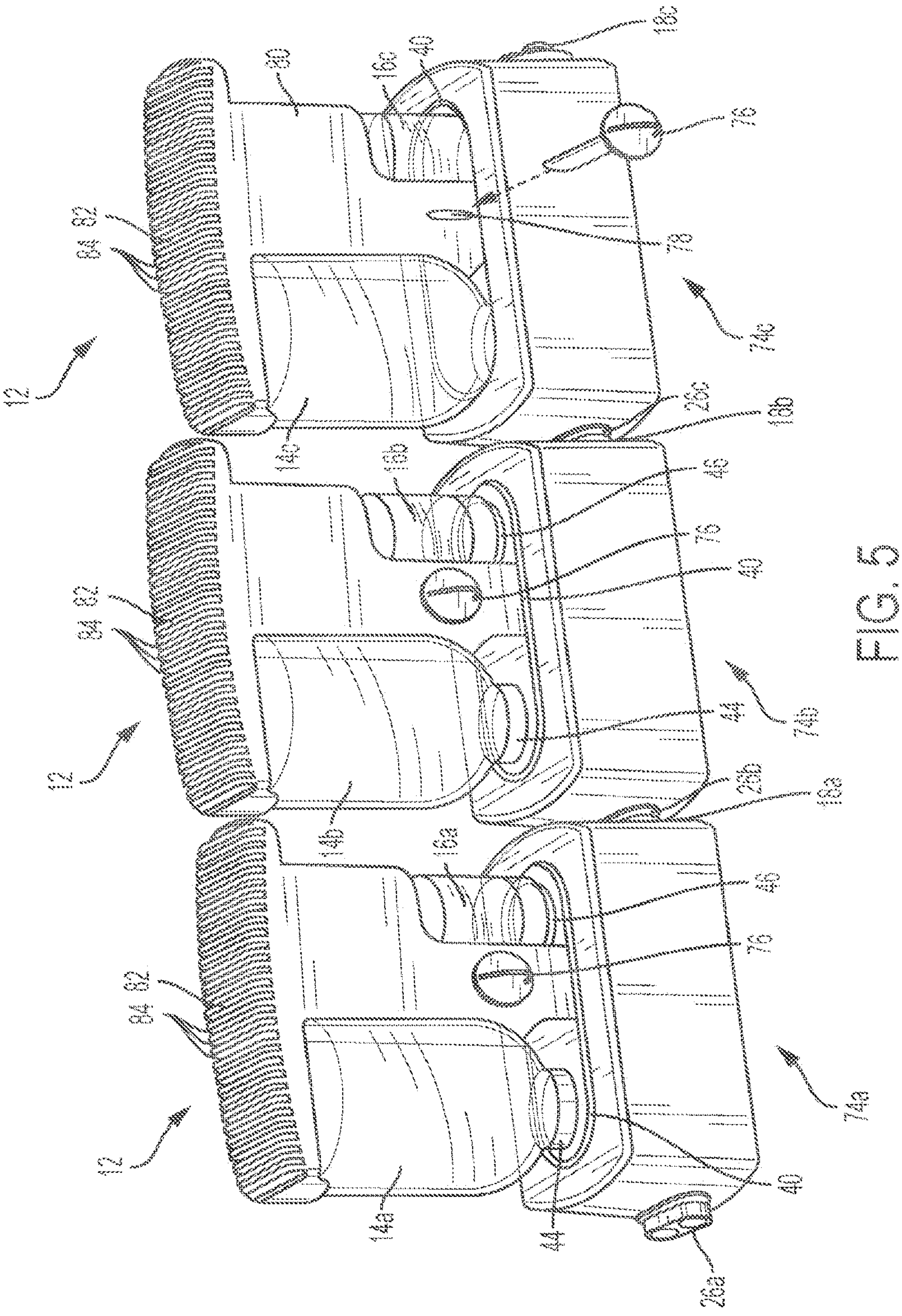
FIG. 5 is a perspective view of the pooling devices of FIG. 4 after connection.
Figure 6:
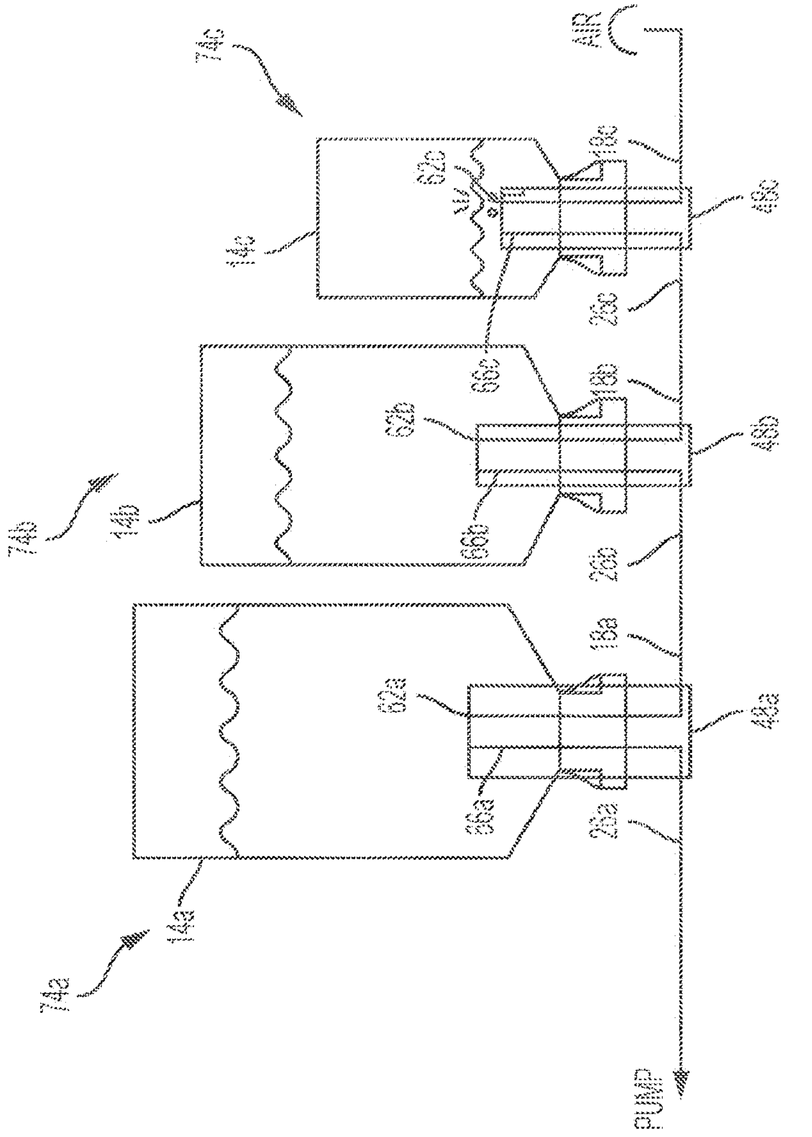
FIG. 6 is a schematic front view of the pooling devices of FIG. 5, featuring an exemplary illustration of a fluid path between the connected medical containers.

Referring now to FIGS. 2 and 4-6, another embodiment of the present pooling device 10 is generally designated 74*a*, 74*b*, 74*c*. In FIGS. 4-6, corresponding components of first, second, and third pooling devices 74*a*, 74*b*, 74*c* are indicated with reference numbers with first three alphabet (i.e., "a," "b," and "c") designations. Components shared with the pooling device 10 are designated with identical reference numbers. In the particular embodiment shown in the pooling device 74*a*, 74*b*, 74*c*, the medical container unit 12 having the first and second containers 14, 16 is attached to the pooling device 74*a*, 74*b*, 74*c* as a pre-assembled unit.

More specifically, the first and second stoppers 44, 46 of the containers 14, 16 are inserted into the cavity 40 of the pooling device 74*a*, 74*b*, 74*c*, and ready to be punctured by the first and second spikes 48, 50 (FIG. 2). In the present pooling device 74*a*, 74*b*, 74*c*, it is contemplated that each device 74 would be terminally sterilized, such as by with gamma radiation or the like, to guarantee a sterile fluid path. The spikes 48, 50 are provided with the protective sheaths 56, that are punctured and compressed as the containers 14, 16 are depressed, thereby keeping the spikes clean and the fluid path sterile until use.

Then, the device 74 and container unit 12 are assembled and sealed into a breathable package and treated with a disinfecting agent, such as hydrogen peroxide vapor or the like, to keep the stoppers 44, 46 and the spikes 48, 50 in a sanitized condition until use.

In this configuration, the first and second stoppers 44, 46 of the containers 14, 16 are pre-staged or pre-positioned in the upper position to be punctured by the first and second spikes 48, 50. However, a lockout mechanism or pin 76 configured for stopping the transition of the container unit 12 from the upper position to the lower position prevents premature activation of the pooling device 74*a*, 74*b*, 74*c* before use (e.g., during shipping and handling). Thus, the pin 76 performs a similar function to the locking clips 58 discussed above. It is contemplated that the lockout pin 76 is inserted into a slot 78 disposed on a body 80 of the container unit 12 between the first and second containers 14, 16, but other suitable configurations of the lockout pin are contemplated.

After the lockout pin 76 is disengaged by pulling it out of the body 80, a press bar 82 having a plurality of grooves 84 for grip enhancing purposes is disposed on a top of the container unit 12, and is pushed downwardly to transition the container unit from the upper position to the lower position. This downward movement of the container unit 12 causes the first and second stoppers 44, 46 of the containers 14, 16 to be punctured by the corresponding first and second spikes 48, 50.

In some embodiments of the present pooling device, as in the depicted embodiments, 74*a*, 74*b*, 74*c*, two or more pooling devices may be serially linked together in a complementary relationship relative to a longitudinal axis of each pooling device for establishing an uninterrupted supply of the medicinal fluid from the linked pooling devices. For example, as illustrated in FIGS. 4 and 5, the inlet port 18*a* of the first pooling device 74*a* is inserted into and complementarily connected with the outlet port 26*b* of the second pooling device 74*b*. In turn, the inlet port 18*b* of the second pooling device 74*b* is inserted into the outlet 26*c* of the third pooling device 74*c* for facilitating an unbroken connection of the fluid path between all linked pooling devices 74*a*, 74*b*, 74*c*.

In this configuration, the first, second, and third pooling devices 74*a*, 74*b*, 74*c* are connected or linked in fluid communication with one another for providing a passageway between the pooling devices for the uninterrupted, continuous delivery of the medicinal fluids. For example, the first medicinal fluids of the linked first containers 14*a*, 14*b*, 14*c* can be administered to the user without interruption or manipulation of the containers. Similarly, the second medicinal fluids of the linked second containers 16*a*, 16*b*, 16*c* can be subsequently administered to the user. It is contemplated that the pooling devices 74*a*, 74*b*, 74*c* can be arranged in any other suitable manner to facilitate the administration of the medical fluids. Further, the first and second medicinal fluids may be delivered to the user in a reverse order to suit the application.

Referring now to FIGS. 5 and 6, an embodiment with a flow path for three linked first containers 14*a*, 14*b*, 14*c* is shown for illustration purposes. In this configuration, ambient air is drawn into the right first container 14*c* via the inlet port 18*c* and the first spike channel 62*c* of the first spike 48*c*. The second spike channel 66*c* of the first spike 48*c* is connected to the first spike channel 62*b* of the first spike 48*b* in the middle first container 14*b*. Similarly, the second spike channel 66*b* of the first spike 48*b* is connected to the first spike channel 62*a* of the first spike 48*a* in the left first container 14*a*.

Next, the second spike channel 66*a* of the first spike 48*a* is connected to the pumping system via the outlet port 26*a* shown on the left of the first container 14*a* in FIG. 6. Another flow path of three linked second containers 16*a*, 16*b*, 16*c* is established in a similar fashion.

In operation, a negative or suction pressure created by the pumping system through the port 26*a* causes an uninterrupted sequential delivery of the first medicinal fluid from three first containers 14*a*, 14*b*, 14*c*. The system 74*a-c* has a built in air/fluid management feature for providing sequential delivery of the medication from the respective containers 14*a-c*. For example, initially, the fluid in the left first container 14*a* is drawn down by the suction pressure applied via the port 26*a* and spike channel 66*a* to the fluid content of the container 14*a* until a vacuum develops above the level of fluid in that container 14*a*. The buildup of this vacuum pressure creates a suction pressure on the fluid content of the container 14*b* via the fluid connection of the spike channel 62*a* and inlet channel 18*a* to the outlet channel 26*b* and spike channel 66*b*.

Next, the suction pressure exerted on the fluid content in the middle first container 14*b* draws down the contents until a similar vacuum develops above the level of fluid in that container. Once the vacuum is developed in both containers 14*a* and 14*b*, a suction pressure is created on the fluid content of the container 14*c* via the fluid connection of the spike channel 62*b* and inlet channel 18*b* to the outlet channel 26*c* and spike channel 66*c*. Since the container 14*c* is vented to ambient through line 18*c*, only a slight vacuum pressure is created above the liquid contents of this container 14*c*. Instead, the created suction pressure will be communicated to ambient via the spike channel 62*c* and inlet port 18*c* and will cause the drawing of air into this container 14*c* and this container will empty first.

The container 14*c* will empty until the liquid level reaches below the entrance to spike channel 66*c*, whereby the interior of next container 14*b* will become exposed to ambient via container 14*c*, allowing the fluid contents of the container 14*b* to be emptied under the suction force of the pumping system. Lastly, after the container 14*b* is emptied, the container 14*a* is then emptied in a similar fashion. Accordingly, three containers 14*a*, 14*b*, 14*c*, are sequentially automatically administered in a distal to proximate order until all of the containers are empty.

Figure 7:
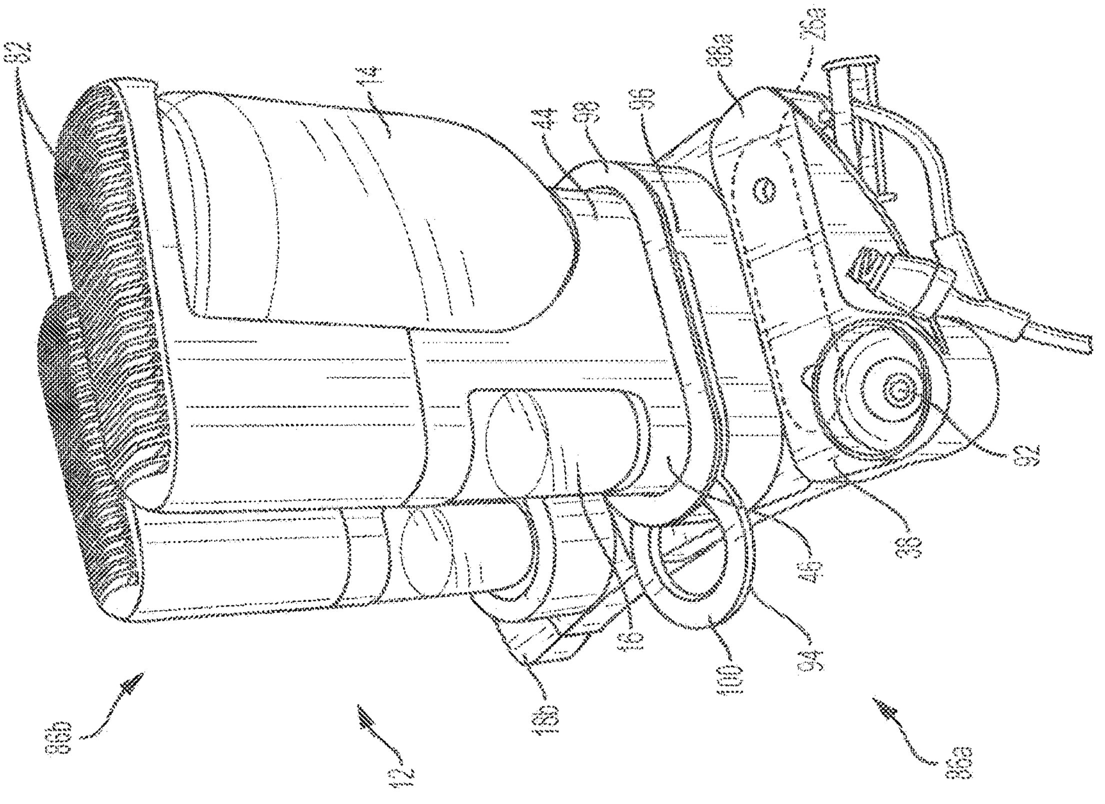
FIG. 7 is a side perspective view of a third embodiment of the present pooling device, illustrating another exemplary arrangement of two connected pooling devices having different configurations for the lockout pin and the inlet and outlet ports.
Figure 8:
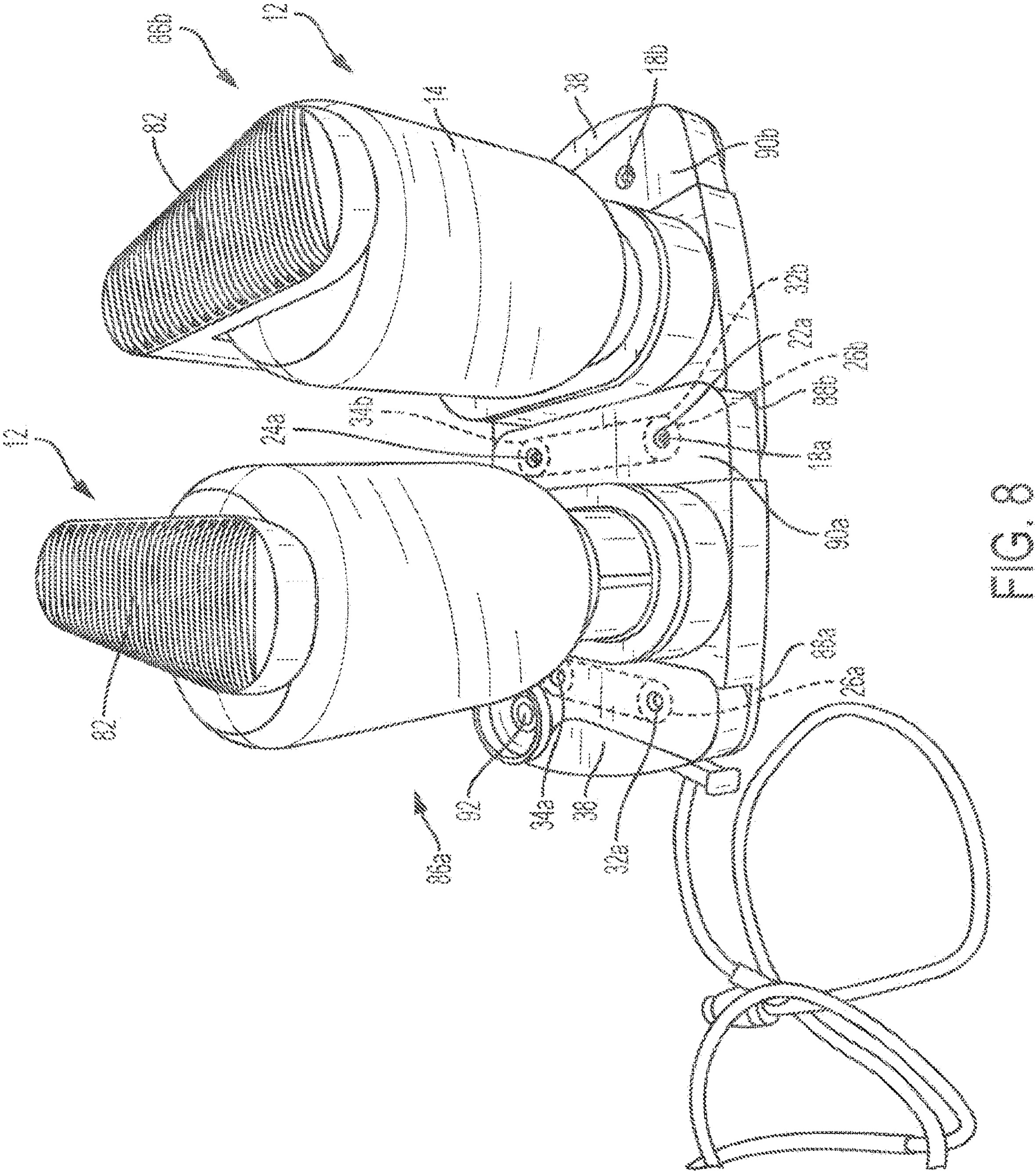
FIG. 8 is a rear perspective view of the pooling devices of FIG. 7 when the adjacent pooling devices are interconnected.
Figure 9:
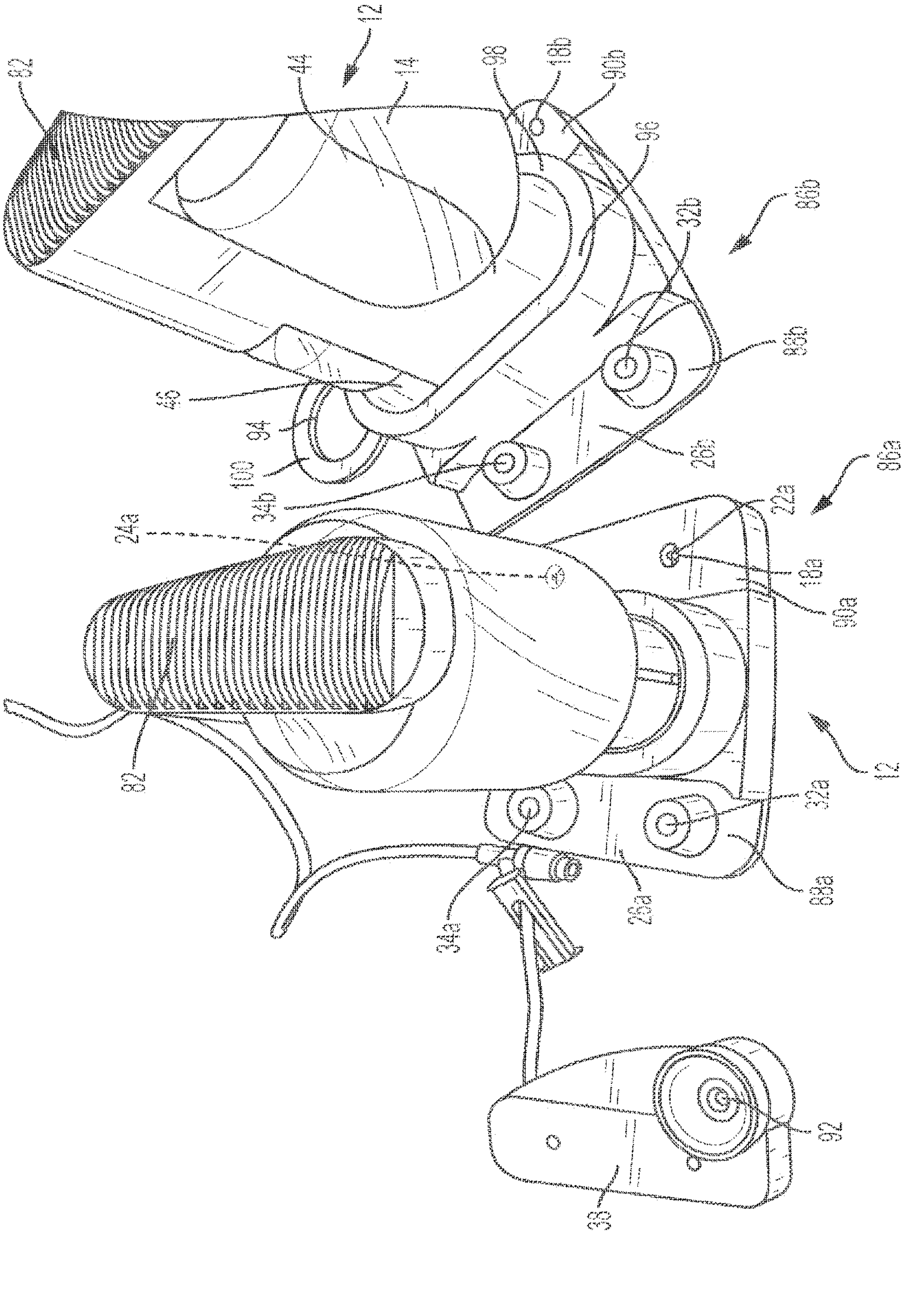
FIG. 9 is a rear perspective view of the pooling device of FIG. 7 when the adjacent pooling devices are disconnected.

A different volumetric amount of each container 14*a*, 14*b*, 14*c* does not affect this sequential fluid delivery process. Exemplary volumetric amounts of standard vials include 25, 50, 100, 200, and 300 milliliters, but any other suitable size or combination of medical containers are contemplated. Referring now to FIGS. 2 and 7-9, yet another (third) embodiment of the present pooling device 74 is generally designated 86*a*, 86*b*. In FIGS. 7-9, corresponding components of first and second pooling devices 86*a*, 86*b* are indicated with reference numbers with first two alphabet (i.e., "a" and "b") designations. Components shared with the pooling device 74 are designated with identical reference numbers. A major difference featured in the pooling devices 86*a*, 86*b* is that the pooling devices are linked or daisy-chained together in a serial arrangement relative to the longitudinal axis of each pooling device.

More specifically, each pooling device 86*a*, 86*b* includes a first or left wing 88*a*, 88*b* configured for accommodating the outlet port 26*a*, 26*b*, and a second or right wing 90*a*, 90*b* configured for accommodating the inlet port 18*a*, 18*b*. As for the first pooling device 86*a* shown in FIG. 9, the first and second inlet channels 22*a*, 24*a* are disposed on the second wing 90*a*, and the first and second outlet channels 32*a*, 34*a* are disposed on the first wing 88*a*. The second pooling device 86*b* has the same configuration for the corresponding inlet and outlet channels.

As illustrated in FIGS. 8 and 9, to establish daisy-chained coupling of two adjacent pooling devices 86*a*, 86*b*, the second wing 90*a* of the first pooling device 86*a* is complementarily connected with the first wing 88*b* of the second pooling device 86*b*. More specifically, in a preferred embodiment, the second wing 90*a* is positioned higher than the first wing 88*b* relative to an axis transverse to a longitudinal axis of the pooling device 86*a*, 86*b*. It is contemplated that the relative positions and configurations of the first and second wings 88*b*, 90*a* can be reversed from the orientation described above.

It is also preferred that the first and second inlet channels 22*a*, 24*a* extend downwardly from a lower surface of the second wing 90*a*, and the first and second outlet channels 32*b*, 34*b* extend upwardly from an upper surface of the first wing 88*b*. Thus, the daisy-chained coupling of the pooling devices 86*a*, 86*b* is achieved by pressing the second wing 90*a* of the first pooling device down onto the first wing 88*b* of the second pooling device, such that the inlet channels 22*a*, 24*a* of the first pooling device are inserted into the outlet channels 32*b*, 34*b* of the second pooling device in a complementary arrangement.

Returning to FIGS. 2, 7 and 9, another feature of the pooling device 86*a*, 86*b* is that the protective cover 38 has an elongate body configured to accommodate a contour or profile of the first and right wings 88*a*, 88*b*, 90*a*, 90*b*. Optionally, the protective cover 38 has an auxiliary port 92 configured for delivering the medicinal fluid from the containers 16*a* and 16*b* through the corresponding outlet port 26*a*, 26*b* into a syringe, for example, docked to the auxiliary port 92. The protective cover 38 also has a tubing set configured for delivering the medical fluid from other containers 14*a* and 14*b* to an infusion pump connected to a patient for infusion. In lieu of the lockout pin 76 (FIG. 5), a locking spacer 94 is provided to prevent the container unit 12 from transitioning to the lower position. Initially, the locking spacer 94 is inserted into a circumferentially extending annular groove 96 disposed on an upper portion 98 of the corresponding pooling device 86*a*, 86*b* to lock the container unit 12 in the upper position.

As similarly operated with the lockout pin 76, after the locking spacer 94 is removed from the pooling device 86*a*, 86*b* by pulling a ring 100 attached to the spacer, the press bar 82 of the container unit 12 is pushed downwardly to transition the container unit from the upper position to the lower position. This downward movement of the container unit 12 causes the first and second stoppers 44, 46 of the containers 14, 16 to be punctured by the corresponding first and second spikes 48, 50.

Figure 10:
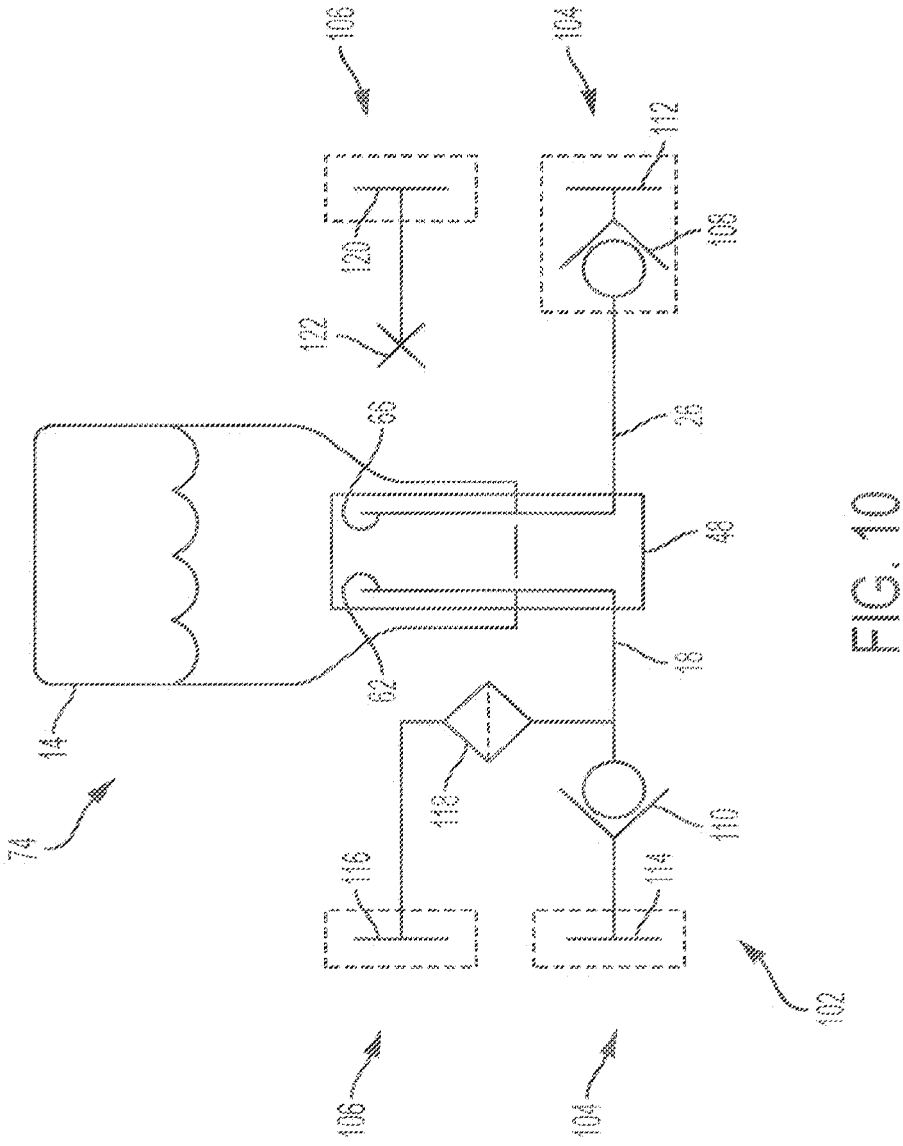
FIG. 10 is a schematic front view of the pooling device of FIG. 5, featuring a leakage prevention mechanism having a fluid connection assembly and an air connection assembly.

Referring now to FIGS. 2, 6, and 10, an exemplary leakage prevention mechanism is generally designated 102, and is designed to prevent unwanted air or fluid leakage from the pooling device 10. Components shared with the pooling device 10 are designated with identical reference numbers. Included in the leakage prevention mechanism 102 are a fluid connection assembly, generally designated 104, configured for controlling a fluid path in the pooling device 10, and an air connection assembly, generally designated 106, configured for controlling an air vent path in the pooling device. It is contemplated that the leakage prevention mechanism 102 is applicable to all embodiments of the pooling devices 10, 74, 86, described above.

In a preferred embodiment, the fluid connection assembly 104 includes a first fluid valve 108 being integrated into the outlet port 26 of the first pooling device 74 for selectively regulating the fluid flow of the medicinal fluid from the first container 14. The first fluid valve 108 is typically closed when not connected to another device or tubing connector, and is mechanically opened to allow the fluid flow via a connector 114 when connected to another device or tubing connector. The fluid connection assembly 104 includes a second fluid check valve 110 being connected to the inlet port 18 of the first pooling device 74 for selectively regulating the directional fluid flow of the medicinal fluid to the first container 14.

It is contemplated that the fluid check valve 110 is one-directional valve allowing the fluid path only toward the first container 14, such that the medicinal fluid in the first container does not leak out of the container when the first and second fluid check valves are in a resting position. The first valve 108 has a first fluid path connector 112 configured for releasably complementarily connecting to the second check valve 110 of another pooling device. Optionally, the second check valve 110 has a second fluid path connector 114 configured for releasably complementarily connecting to the first check valve 108 of another pooling device.

During use, the first fluid valve 108 prevents the fluid flow from the first container 14 when the pooling device 74 is not connected to another pooling device. The valve is mechanically opened to allow free fluid flow when connected to another device 74. The second fluid check valve 110 prevents leakage from the connector 114 when the device 74 is not connected to another pooling device, and also prevents unwanted leakage between connected pooling devices 74. An exemplary cracking pressure of the fluid check valve 110 is approximately 3-5 pounds per square inch (PSI) to allow the valve to be opened by fluid pressure created by a connected pump.

For selectively regulating a directional air flow of the pooling device 74, the air connection assembly 106 includes an air path connector 116 being connected to the inlet port 18 of the first pooling device 74 via a hydrophobic filter 118. Specifically, the hydrophobic filter 118 is connected at one end to the air path connector 116, and at an opposite end to the spike 48 downstream of the fluid check valve 110. As known in the art, the hydrophobic filter 118 allows air passage, but prevents fluid from traveling through the filter. Thus, the hydrophobic filter 118 prevents unwanted leakage of the medicinal fluid from the air path connector 116. Alternatively, other suitable hydrophilic filters are also contemplated to suit different applications.

An air path plug or end component 120 having a blind cavity 122 is provided in the air connection assembly 106, and is configured for releasably complementarily connecting to the air path connector 116 of another pooling device. When the air path plug 120 and the air path connector 116 are matingly or complementarily connected, the air vent path in the pooling device 74 is obstructed or blocked by the blind cavity 122, thereby effectively preventing air leakage.

Figure 11:
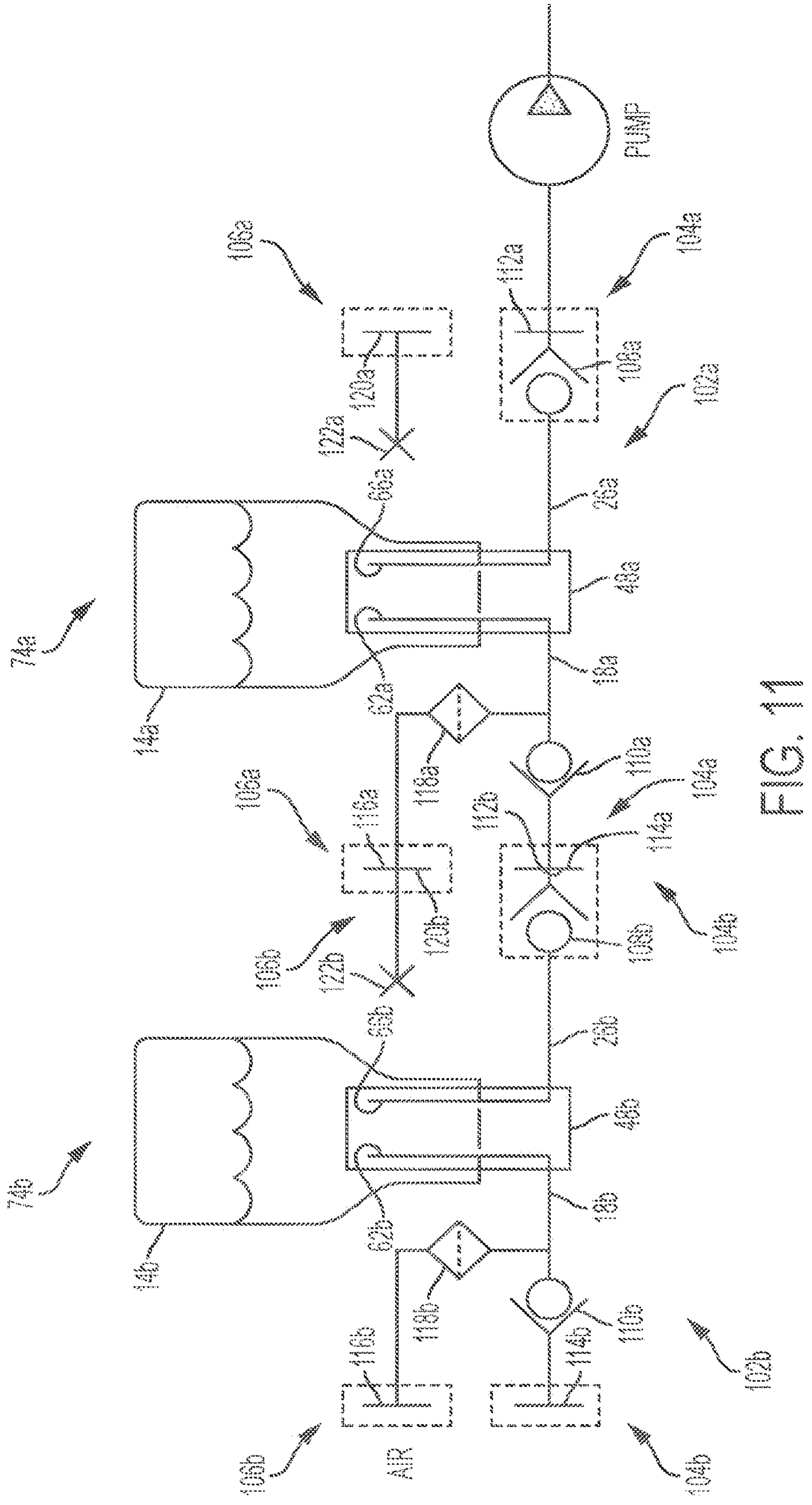
FIG. 11 is a schematic front view of the pooling devices of FIG. 10 when the adjacent pooling devices are interconnected via the leakage prevention mechanism.

Referring now to FIGS. 2, 6, and 11, it is contemplated that the first pooling device 74*a* is linked or daisy-chained to the second pooling device 74*b* (FIG. 11). Corresponding components of the leakage prevention mechanism 102*a*, 102*b* and the first and second pooling devices 74*a*, 74*b* are indicated with reference numbers with first two alphabet (i.e., “a” and “b”) designations. In this configuration, the air path plug 120*b* of the second air connection assembly 106*b* is matingly or complementarily connected to the air path connector 116*a* of the first air connection assembly 106*a*. Thus, when the first and second pooling devices 74*a*, 74*b* are linked or daisy-chained, the air vent paths of the connected pooling devices are automatically closed or blocked except the air vent path of the most distal device of the daisy-chained devices (e.g., the air vent path defined by the air path connector 116*b* of the second air connection assembly 106*b*).

As for the fluid path, the first fluid path connector 112*b* of the first fluid valve 108*b* of the second fluid connection assembly 104*b* is matingly or complementarily connected to the second fluid path connector 114*a* of the second fluid check valve 10*a* of the first fluid connection assembly 104*a*. It is also contemplated that the pumping system is connected to the first fluid path connector 112*a* of the first fluid valve 108*a* of the first fluid connection assembly 104*a* in fluid communication with the container 14*a*.

In this configuration, the connected first valves 108*a*, 108*b* are mechanically opened by the first fluid path connectors 112*a*, 112*b* for allowing the fluid communication between the pumping system and the pooling devices 74*a*, 74*b*. However, neither of the second check valves 110*a*, 110*b* needs to be mechanically opened because the fluid flow from the second pooling device 74*b* to the first pooling device 74*a* is already accommodated by the one-directional second check valve 110*a*. Only the first valves 108*a*, 108*b* that do not allow the fluid flow out of the containers 14*a*, 14*b* are mechanically opened.

As described similarly above, ambient air is drawn into the container 14*b* of the second pooling device 74*b* via the air path connector 116*b* and the hydrophobic filter 118*b* of the air connection assembly 106*b*. Simultaneously, the second check valve 110*b* of the second fluid connection assembly 104*b* of the second pooling device 74*b* prevents the fluid leakage from the container 14*b*. As a result, the negative pressure, such as vacuum, created by the pumping system causes an uninterrupted sequential delivery of the medicinal fluids from the containers 14*a*, 14*b* without any unwanted fluid leakage.

Figure 12:
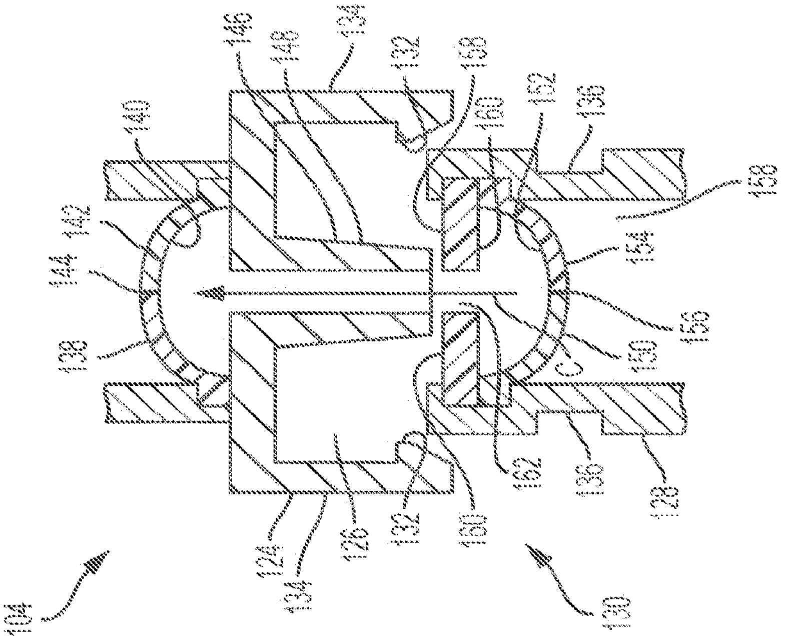
FIG. 12 is an exploded, fragmentary vertical cross-section of the fluid connection assembly of FIG. 10.

Referring now to FIGS. 10 and 12, it is preferred that the fluid connection assembly 104 includes a female member 124 having a female member opening 126 configured for accommodating the insertion of a male member 128 of the fluid connection assembly. For securely attaching the female member 124 to the male member 128, a snap-fit assembly locking mechanism, generally designated 130, is provided in the fluid connection assembly 104, and configured for releasably connecting the female and male members 124, 128 together.

In a preferred embodiment, the locking mechanism 130 includes at least one locking tab or protrusion 132 being disposed on an inner surface of a side wall 134 of the female member 124, and at least one indent or groove 136 being disposed on an outer surface of the male member 128. When the male member 128 is slidingly inserted into the female member opening 126, the locking tab 132 and the corresponding indent 136 of the locking mechanism 130 are matingly latched for securely holding the female and male members 124, 128 in place, thereby initiating the directional fluid flow of the medicinal fluid, as designated by an arrow C. Other locking mechanism structures, such as annular locking and releasing grooves, lateral wings, and the like, are contemplated.

An important aspect of the fluid connection assembly 104 is that the female member 124 has a first sealing fixture 138 attached to an outer upper surface of the female member for providing a fluid-tight compression seal. It is contemplated that the first sealing fixture 138 has a first concave side 140 and an opposite first convex side 142, and the seal is designed to be opened when a pressure is applied against the first concave or convex side 140, 142. Preferably, the first sealing fixture 138 has a substantially dome shape, and is made of a flexible, elastomeric material. It is contemplated that a first slit or gap 144 having a predetermined length is disposed at a substantially center of the first sealing fixture 138, such that the slit is tightly closed at rest but opened when the pressure is applied against the first concave or convex side 140, 142.

More specifically, the first slit 144 of the first sealing fixture 138 prevents the fluid flow of the medicinal fluid when the first sealing fixture is in a resting position. However, when the negative pressure created by the pumping system is applied to the convex side 142 of the first sealing fixture 138, the first slit 144 is opened to allow the fluid flow of the medicinal fluid, as designated by the arrow C. Other suitable types of check valves, such as spring-loaded ball check valves, duckbill valves, umbrella valves, diaphragm valves, or the like, are contemplated to suit the application.

It is also contemplated that the female member 124 has a tubular column 146 depending from a substantially center of an inner upper surface of the female member 124 within the female member opening 126 along a longitudinal axis of the female member. Preferably, the tubular column 146 has an inclined or sloped outer surface 148 with a lead-in geometry, resulting in a funnel shaped outer wall. Specifically, an outer diameter of the tubular column 146 is gradually increased toward the inner upper surface of the female member 124. Other suitable geometric shapes, such as square, rectangular, hexagonal shapes, are also contemplated for the column 146.

Another important aspect of the fluid connection assembly 104 is that the male member 128 is substantially tubular and has a second sealing fixture 150 attached to an inner surface of the male member for providing the fluid-tight compression seal. As with the first sealing fixture 138, the second sealing fixture 150 has a second concave side 152 and an opposite second convex side 154. As described above, the second sealing fixture 150 has the same configuration of the first sealing fixture 138, and operates the same way as the first sealing fixture. However, it is noted that the first and second sealing fixtures 138, 150 are disposed in opposite orientations for preventing the fluid leakage from the fluid connection assembly 104.

More specifically, the first sealing fixture 138 is disposed on the outer upper surface of the female member 124, such that the first convex side 142 is faced upwardly along a longitudinal axis of the female member in a fluid flow direction, as designated by the arrow C. In contrast, the second sealing fixture 150 is disposed on the inner surface of the male member 128, such that the second convex side 154 is faced downwardly along a longitudinal axis of the male member against the fluid flow direction, as designated by the arrow C. Thus, at rest, a second slit or gap 156 of the second sealing fixture 150 prevents the fluid flow of the medicinal fluid from the male member 128, and the first slit or gap 144 of the first sealing fixture 138 prevents the fluid flow of the medicinal fluid from the female member 124.

It is also contemplated that the male member 128 has a female member opening 158 configured for accommodating the insertion of the tubular column 146 of the female member 124. An elastomeric backup washer 160 having a central throughbore 162 is disposed near an upper end of the inner surface of the male member 128. Since the central throughbore 162 of the backup washer 160 is dimensioned to accommodate the insertion of the tubular column 146 of the female member 124, an inner diameter of the throughbore is slightly smaller than a smallest outer diameter of the tubular column. Thus, as the tubular column 146 of the female member 124 is gradually inserted into the central throughbore 162 of the backup washer 160, a fluid-tight interference-fit is formed between the tubular column and the backup washer. As the tubular column 146 is completely inserted, it forces open the slit 156 and allows fluid communication between the female member 124 and the male member 128.

Figure 13:
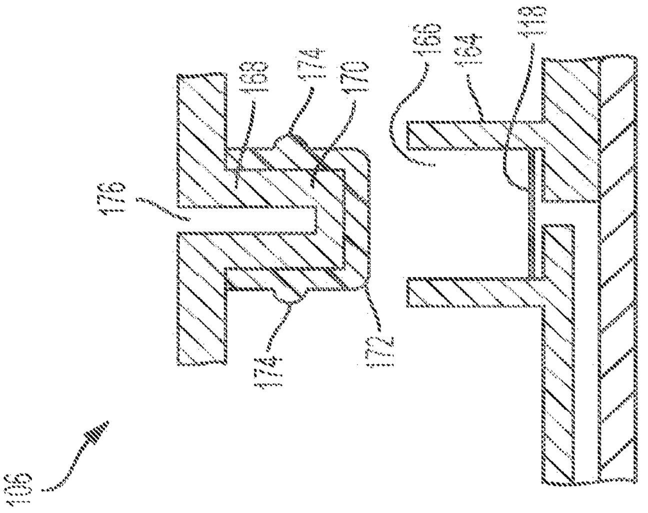
FIG. 13 is an exploded, fragmentary vertical cross-section of the air connection assembly of FIG. 10.

Referring now to FIGS. 10 and 13, it is preferred that the air connection assembly 106 includes a female member 164 having a female member opening 166 configured for accommodating the insertion of a male member 168 of the air connection assembly. An important aspect of the female member 164 of the air connection assembly 106 is that the hydrophobic filter 118 is disposed near a lower end of an inner surface of the female member 164. For example, the hydrophobic filter 118 is attachable to the inner surface of the female member 164 by chemical adhesives, solvent boding, ultrasonic welding or other conventional fastening techniques.

A rigid cylindrical body 170 of the male member 168 is enclosed with a flexible, elastomeric sheath 172 having an annular protrusion 174, such that as the male member 168 is gradually inserted into the female member opening 166, the annular protrusion creates an air-tight interference fit between the sheath and the female member 164. Thus, it is preferred that an outer diameter of the annular protrusion 174 is slightly greater than an inner diameter of the female member opening 166. Although a hollow inner portion 176 of the male member 168 is shown for illustration purposes, any suitable solid or semi-solid material can be separately inserted into or integrally formed with the inner portion of the male member to suit the application.

Figure 14:
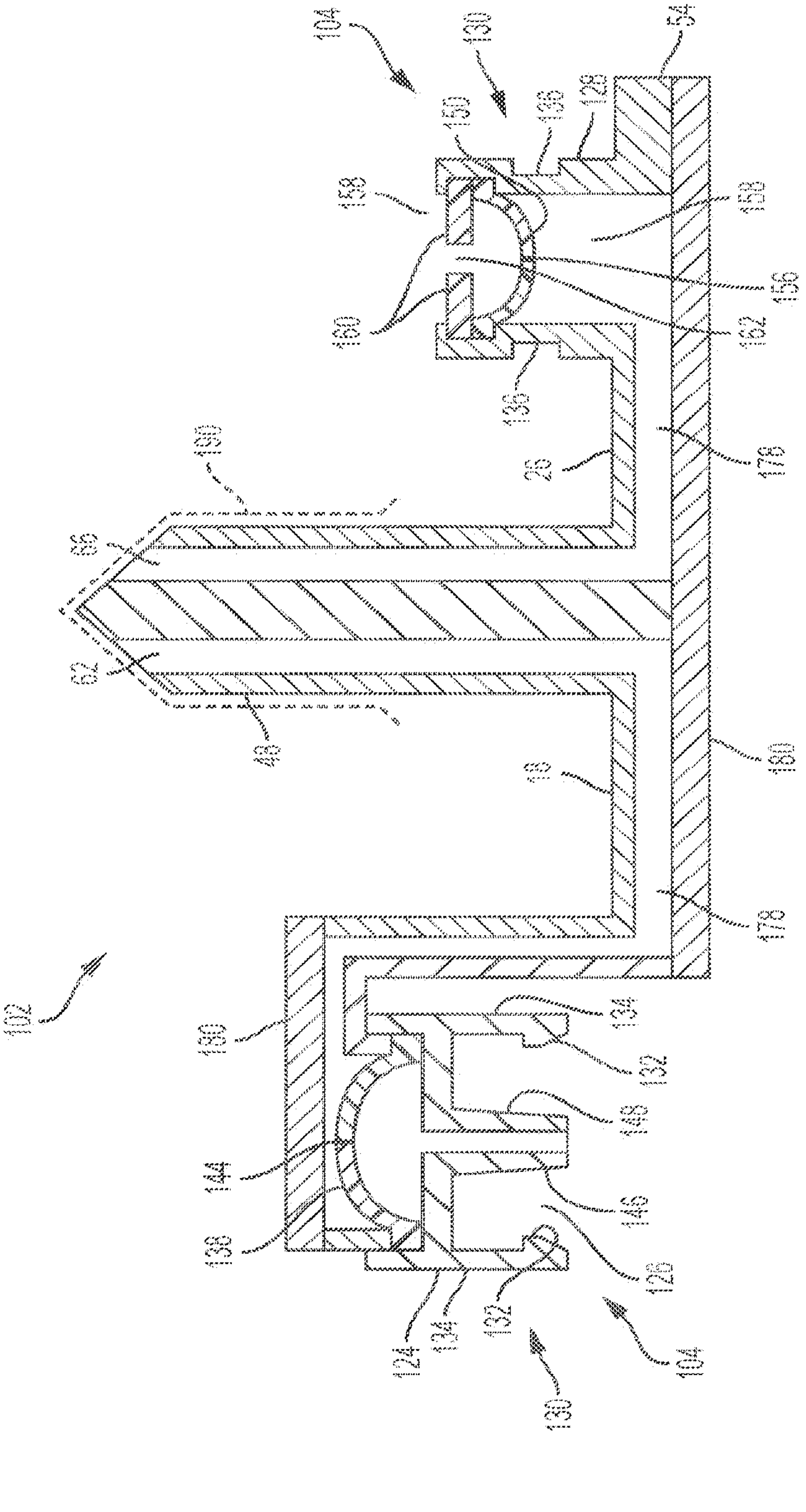
FIG. 14 is a vertical cross-section of the leakage prevention mechanism of FIG. 10, illustrating a fluid path of the fluid connection assembly.
Figure 15:
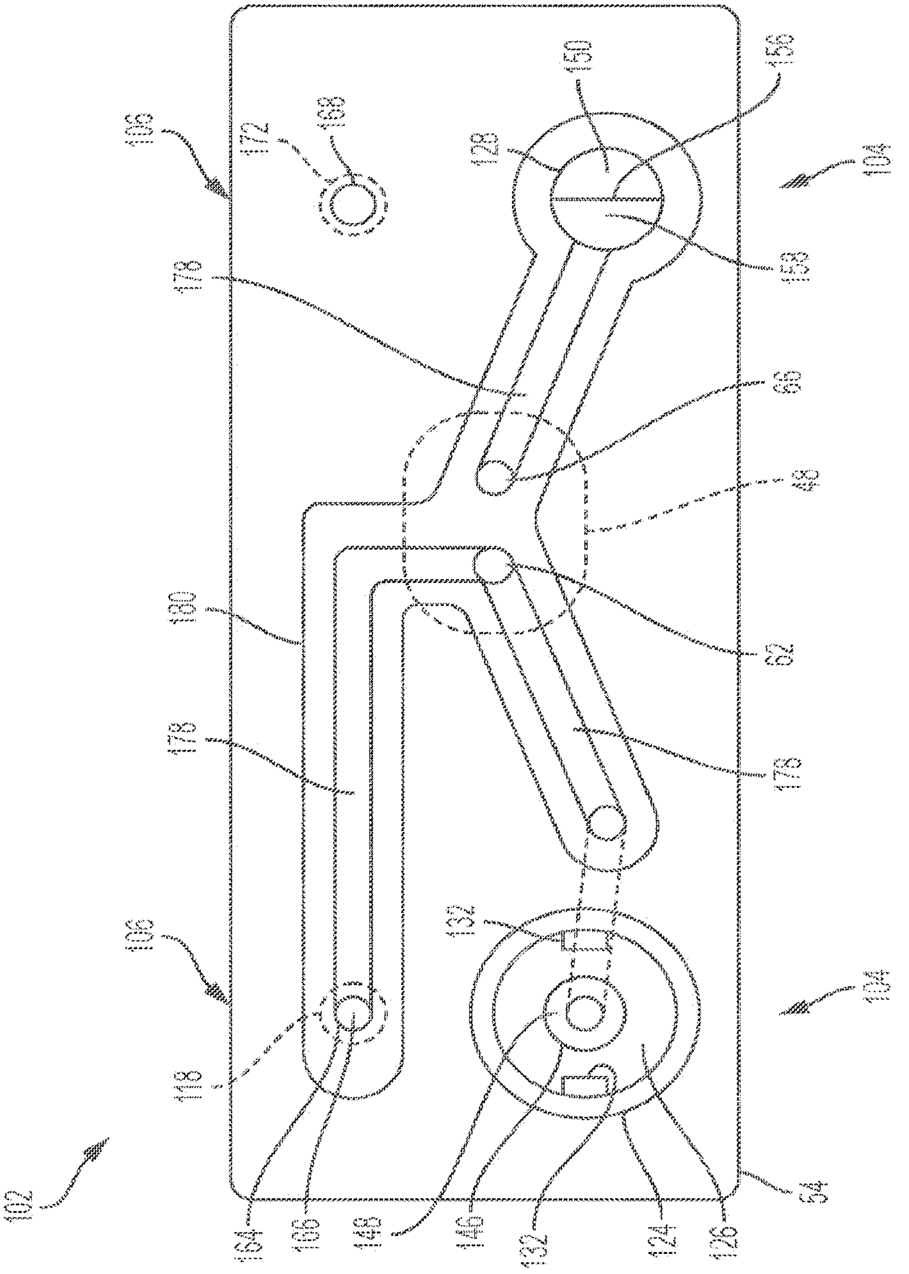
FIG. 15 is a bottom view of the leakage prevention mechanism of FIG. 10.
Figure 16:
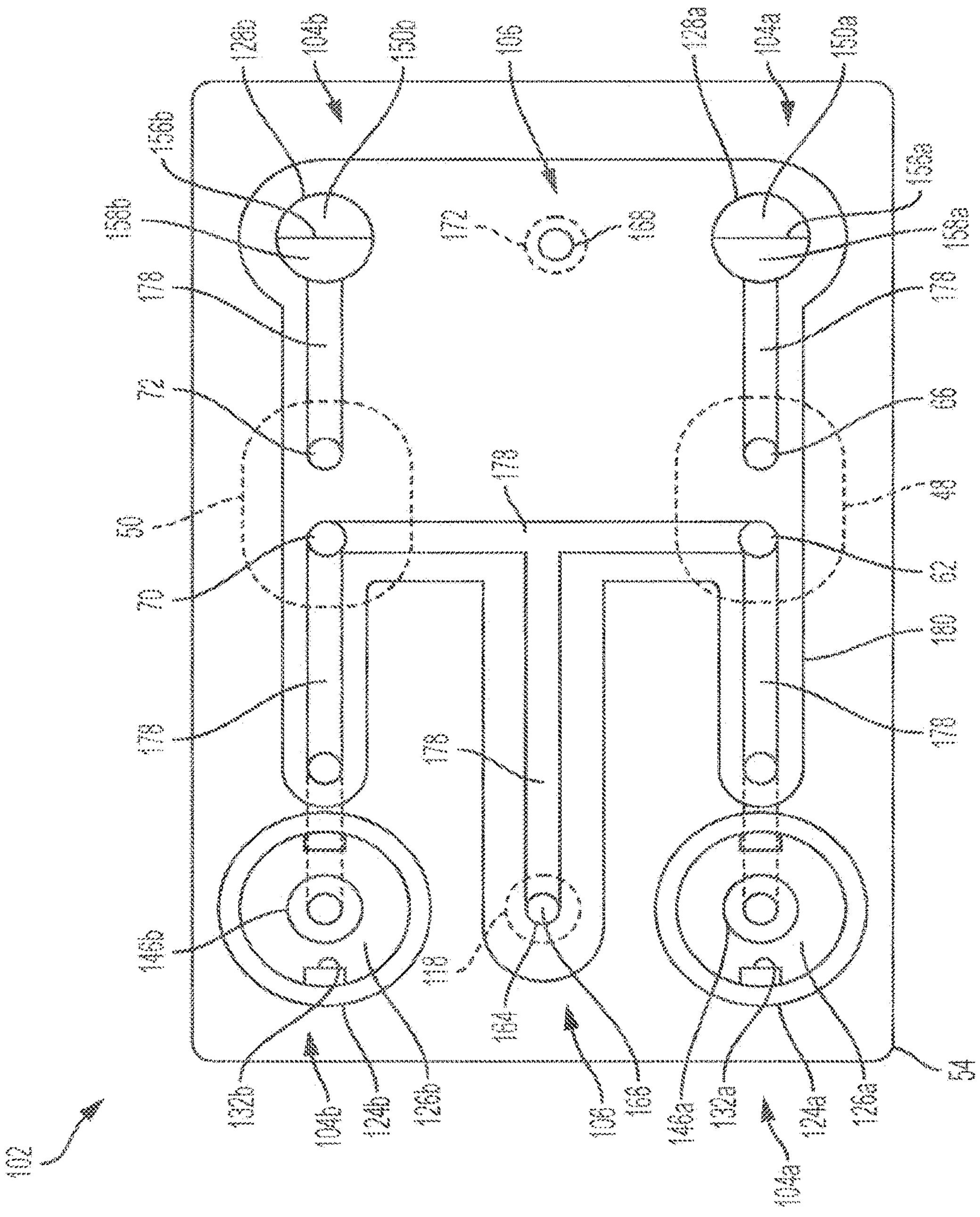
FIG. 16 is a bottom view of the leakage prevention mechanism of FIG. 10, configured for facilitating the dual medical container unit.

Referring now to FIGS. 2, 10-12, and 14, an exemplary fluid path of the fluid connection assembly 104 is illustrated in FIG. 14. As discussed above, it is contemplated that the pumping system is connected to the male member 128 of the fluid connection assembly 104. The pumping system would have a tubing set with a female connector 124 similar to the one on the pooling devices. When the tubing set with the female connector 124 is connected to a pooling device, the tubular column 146 inside of the female connector 124 will force open the slit 156 in the male connector 128 of the pooling device, thereby allowing the fluid flow of the medicinal fluid from the medical container 14 via the second spike channel 66 and the outlet port 26.

When the female member 124 of the fluid connection assembly 104 is connected to the male member 128 of another adjacent pooling device 74, the negative pressure causes the first sealing fixture 138 of the female member to open. As a result, the medicinal fluid from the adjacent pooling device will flow into the medical container 14 via the first spike channel 62 and the inlet port 18, for establishing the uninterrupted supply of the medicinal fluid from the linked or daisy-chained pooling devices. It is contemplated the sealing fixtures 138, 150 and the washer 160 are made of flexible, resilient materials, such as synthetic resin or plastic, rubber, or the like. Other suitable materials are also contemplated to suit the application.

It is contemplated that the fluid path of the medicinal fluid of the pooling device 74 is incorporated into an injection molded assembly as an integral unit. For example, in some embodiments, the male member 128 of the fluid connection assembly 104 is preferably integrally transversely attached to the base 54 of the pooling device 74, such that the male member projects normally from the base. In this configuration, as similarly shown in FIGS. 8 and 9, when the female and male members 124, 128 are connected to each other, an enhanced secure coupling of linked pooling devices is achieved, thereby preventing from an unwanted disassembly of the linked devices. It is also contemplated that the relative positions and configurations of the female and male members 124, 128 can be reversed from the orientation described above.

Referring now to FIGS. 10-12, 14, and 15, it is contemplated that a plurality of fluid and air path grooves 178 are molded into the base 54 of the pooling device 74 for forming at least a portion of the fluid path of the medicinal fluid. In this configuration, the inlet port 18 and the outlet port 26 are integrated into the grooves 178 as a single unit, so that the fluid and air paths from the spike 48 to the fluid and air connection assemblies 104, 106 are seamlessly transitioned.

More specifically, as for the fluid path, the female member opening 126 of the female member 124 of the fluid connection assembly 104 is connected to the first spike channel 62 of the spike 48 via the groove 178 in fluid communication with the medical container 14, and the second spike channel 66 of the spike 48 is connected to the male member opening 158 of the male member 128 of the fluid connection assembly using another groove, thereby forming a continuous fluid path from the female member 124 to the male member 128.

As for the air vent path, the female member opening 166 of the female member 164 of the air connection assembly 106 is connected to the first spike channel 62 of the spike 48 via the groove 178 in fluid communication with the medical container 14, such that the ambient air is drawn into the medical container 14 when the female member of the air connection assembly is not plugged by the male member 168 of the air connection assembly.

In some embodiments, a protective plate 180 (FIG. 14) is used to cover and seal the fluid and air paths defined by the grooves 178. Attachment of the plate 180 to the base 54 is achieved by chemical adhesives, solvent boding, ultrasonic welding or other conventional fastening techniques. A shape of the plate 180 is variable depending on the shapes of the grooves, but other suitable geometric shapes, such as square, rectangular, or oval shapes, are contemplated to suit the application.

Referring now to FIGS. 1, 2, 14, and 16, another exemplary layout of the grooves 178 of the leakage prevention mechanism 102 is illustrated wherein the grooves are constructed and arranged for facilitating the dual medical container unit 12. Corresponding components of the fluid connection assembly 104 are indicated with reference numbers with first two alphabet (i.e., "a" and "b") designations. An important aspect of this groove configuration is that although two separate or distinct fluid connection assemblies **104*a*, 104*b* are included in the leakage prevention mechanism 102, only one air connection assembly 106 is included and shared by the first and second spikes 48, 50**.

Specifically, the female member opening 166 of the female member 164 of the air connection assembly 106 is connected to both the first spike channel 62 of the first spike 48 and the first spike channel 70 of the second spike 50 via the grooves 178, such that the ambient air received through the female member of the air connection assembly flows simultaneously into both the first and second medical containers 14, 16. While a "T"-shaped air vent path layout of the grooves 178 is shown for illustration purposes, other suitable arrangements, such as "Y"- and "V"-shaped layouts, are also contemplated to suit the application.

Referring now to FIGS. 2, 10A-10C and 14, it is also contemplated that the fluid connection assembly 104 includes a first force-activated valve 182 (FIG. 10A) being connected to the outlet port 26 of the pooling device 74 for selectively regulating a directional fluid flow of the fluid. In a similar configuration, the fluid connection assembly 104 includes a second force-activated valve 184 (FIG. 10A) being connected to the inlet port 18 of the pooling device 74 for selectively regulating the directional fluid flow of the fluid.

Figure 10A:
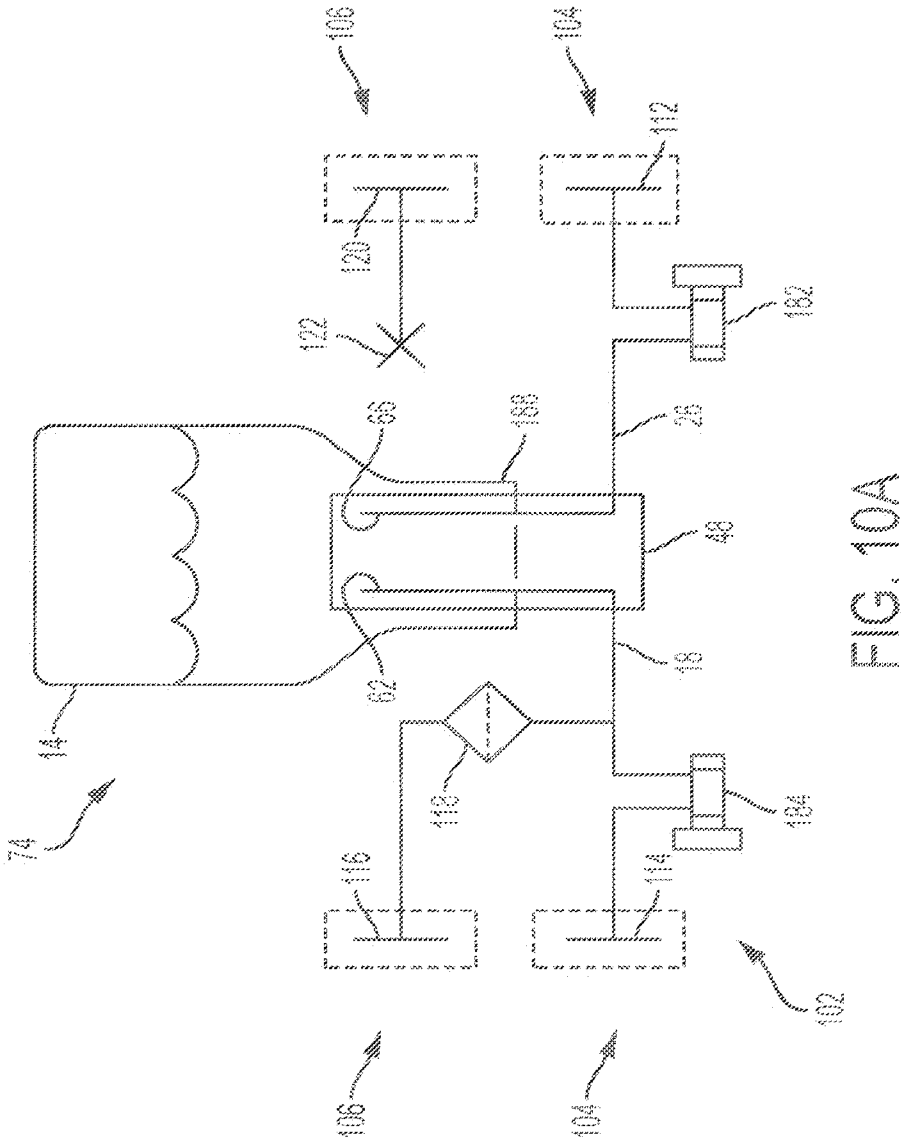
FIG. 10A is a schematic front view of the leakage prevention mechanism of FIG. 10 featuring an exemplary combination of two force-activated values.
Figure 10B:
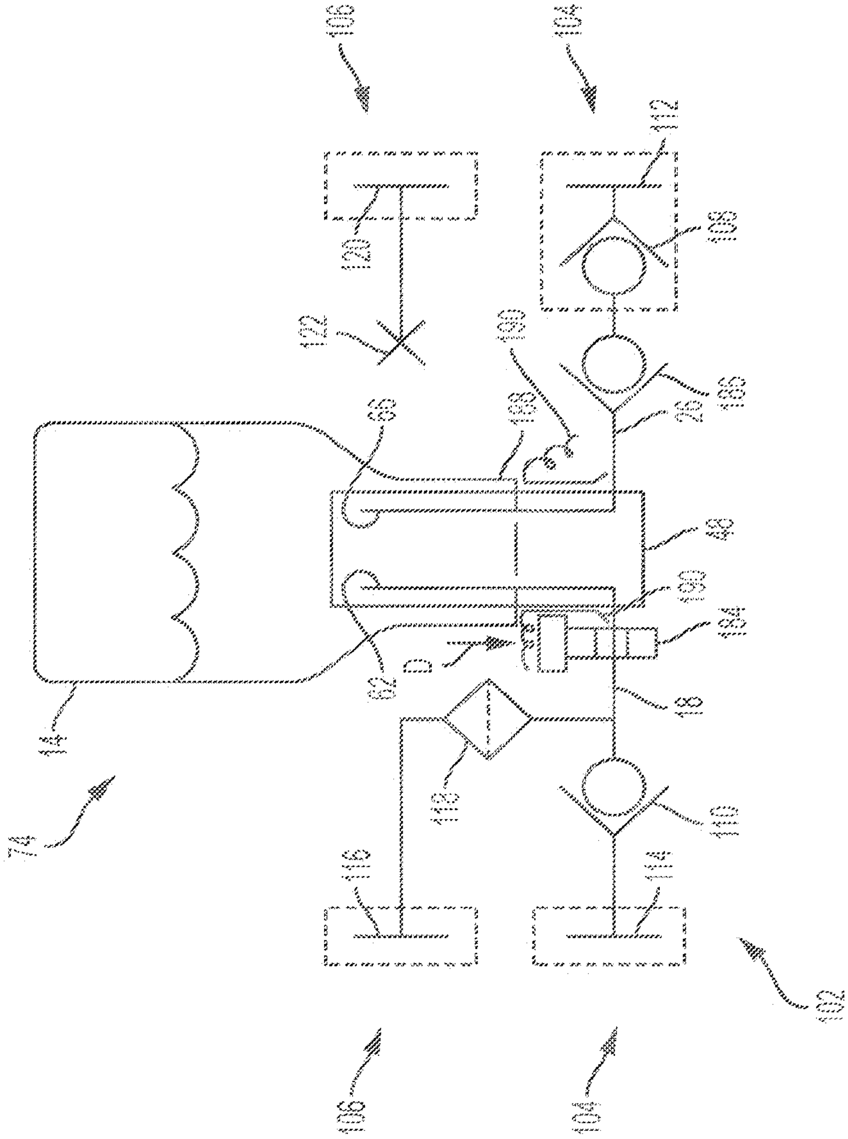
FIG. 10B is a schematic front view of the leakage prevention mechanism of FIG. 10, featuring an exemplary combination of a force-activated valve and a unidirectional check valve.

For example, as illustrated in FIG. 10B, the second force-activated valve 184 is disposed between the second fluid check valve 110 and the first spike 48, and connected to the inlet port 18, such that the fluid flow from the connector 114 is controlled by operation of the second force-activated valve, for preventing the fluid leakage from the fluid connection assembly 104. It is preferred that a unidirectional check valve 186 is connected to at least one of the inlet port 18 and the outlet port 26 of the pooling device 74 for selectively regulating the directional fluid flow of the fluid.

Specifically, to activate the second force-activated valve 184 and thus allow the fluid flow in the inlet port 18, the first medical container 14 is pushed downwardly to transition the first medical container from the upper position to the lower position, as designated by an arrow D (FIG. 10B). This downward movement of the first medical container 14 causes a top portion 188 of the first medical container 14 to depress the corresponding force-activated valve 184 and allow the fluid flow from the connector 114. Conversely, when the second force-activated valve 184 is not activated, the fluid flow is prevented in the inlet port 18. Other suitable locations along the fluid or air flow connecting to the inlet port 18 and the outlet port 26 are also contemplated to suit different applications.

Similarly, the activation of the first or second force-activated valve 182, 184 shown in FIG. 10A is achieved by matingly or complementarily interconnecting the first fluid path connector 112 of the fluid connection assembly 104 of the pooling device 74 to the second fluid path connector 114 of the fluid connection assembly 104 of another pooling device. As discussed above, an exemplary interconnection of two adjacent pooling devices 74*a*, 74*b* is shown in FIG. 11.

It is also contemplated that at least one of the spikes 48, 50 is enclosed with a spike sheath 190 (shown in phantom in FIG. 14) configured for connecting the inlet and outlet ports 18, 26 of the pooling device 74 in fluid communication. For example, in an initial position, the spike sheath 190 simultaneously and securely encloses the first spike channel 62 and the second spike channel 66 of the first spike 48, thereby allowing the air flow or the fluid flow between the inlet and outlet ports 18, 26 of the pooling device 74.

However, as shown in FIG. 10B, the spike sheath 190 is puncturable and compressible as the container 14 is depressed. As discussed above, when the first medical container 14 transitions from the upper position to the lower position, as designated by the arrow D, the spike sheath 190 is also pushed downwardly by the top portion 188 of the container 14 from the upper position shown in FIG. 14 to the lower position shown in FIG. 10B. By this movement of the container 14, the spike sheath 190 is broken, and the fluid flow between the inlet and outlet ports 18, 26 is achieved.

Figure 10C:
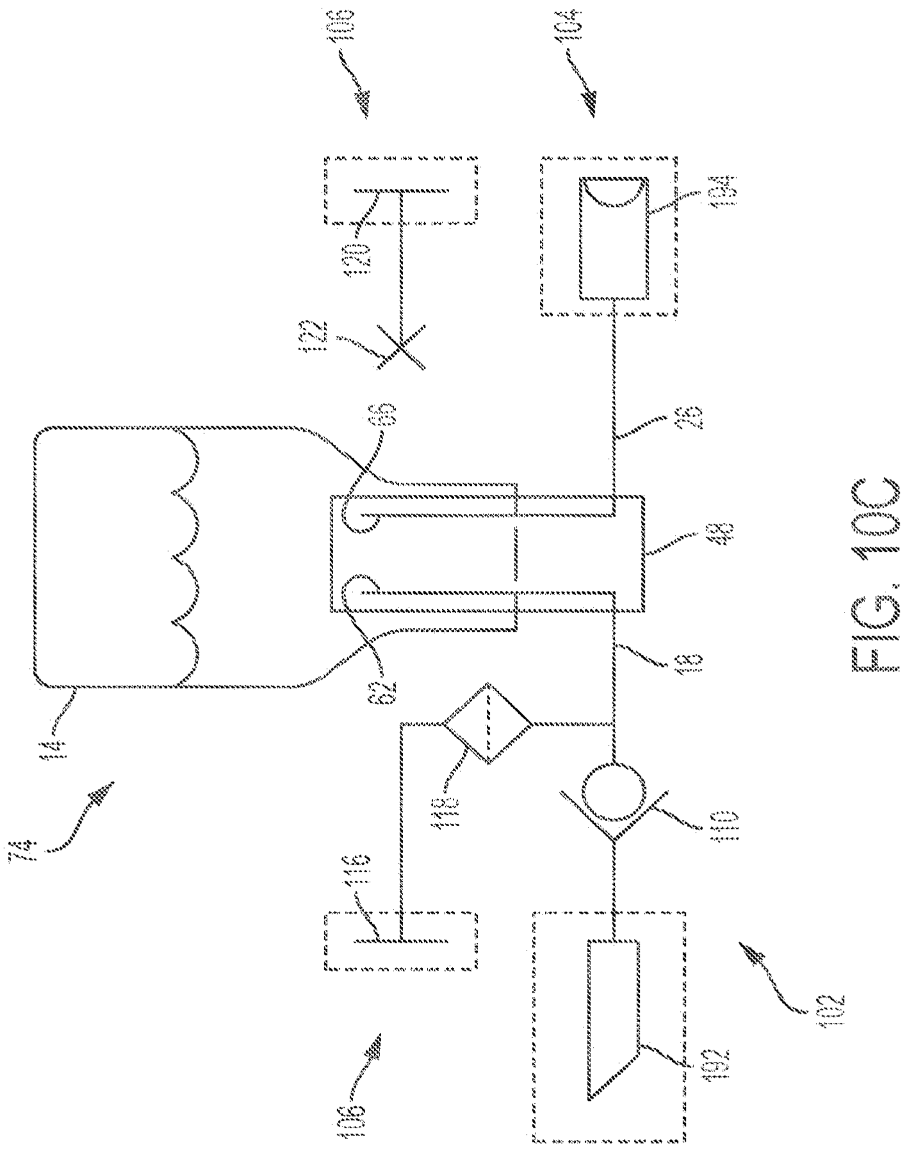
FIG. 10C is a schematic front view of the leakage prevention mechanism of FIG. 10, featuring an exemplary combination of a spike connector and an access dome valve.

Referring now to FIGS. 10C and 14, the fluid connection assembly 104 includes a spike connector 192 and an access dome valve 194. It is preferred that the spike connector 192 is connected to the inlet port 18 of the pooling device 74, and the access dome valve 194 is connected to the outlet port 26 of the pooling device. As described above, the access dome valve 194 has the configuration similar to the second sealing fixture 150 of the snap-fit locking mechanism 130 shown in FIG. 14. In this configuration, the access dome valve 194 has the opening or throughbore 162 configured for accommodating insertion of the spike connector 192 in a complementary relationship.

Figure 17A:
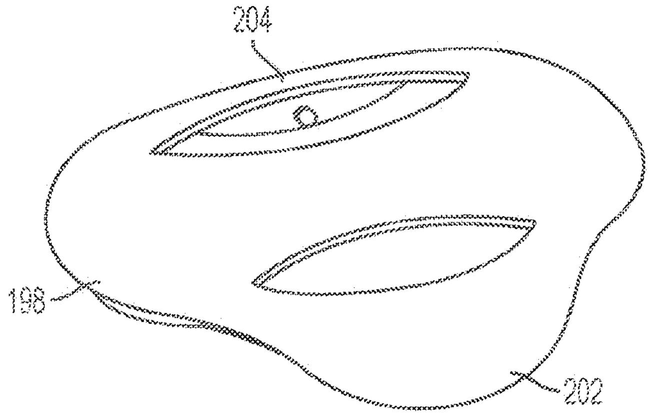
FIG. 17A is a top perspective view of an exemplary cap remover designed to be used with the pooling device of FIG. 1
Figure 17B:
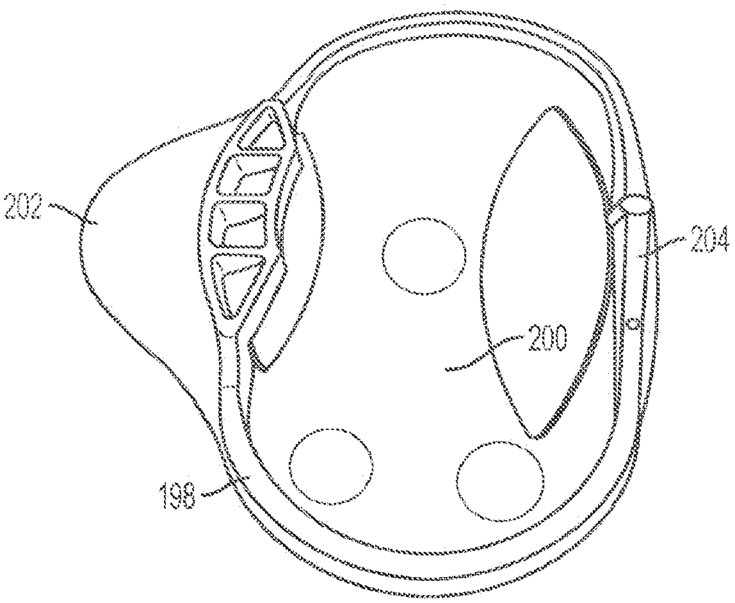
FIG. 17B is a bottom perspective view of the cap remover of FIG. 17A.
Figure 17C:
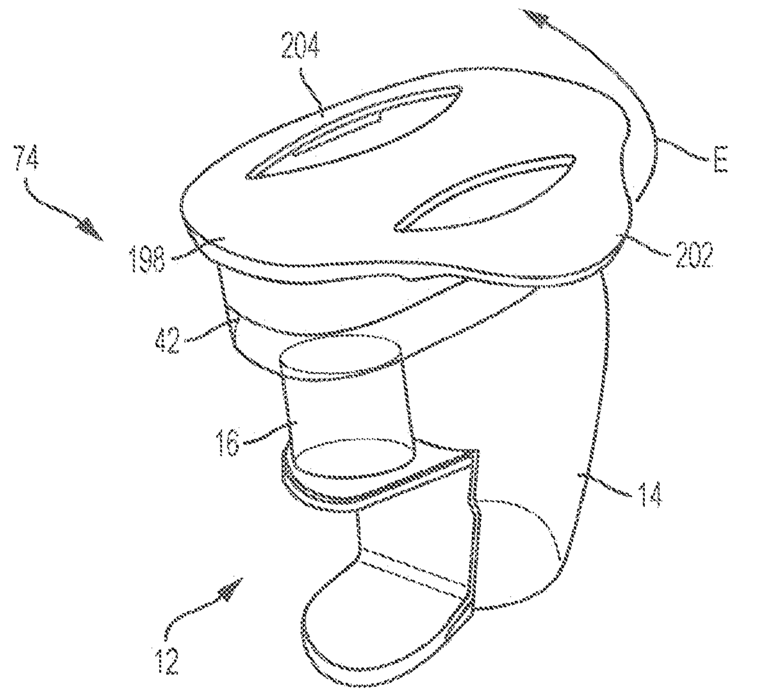
FIGS. 17C-17D illustrate exemplary uses of the cap remover of FIG. 17A.

Referring now to FIGS. 1, 8, and 17A-17D, the pooling device 74 includes a cap remover 198 attached to at least one of the pooling devices and configured for removing the top cap 42 of the corresponding container. In a preferred embodiment, the cap remover 198 includes a central cavity 200 having a head region 202 and a tail region 204, wherein the head and tail regions are disposed, preferably inwardly, in opposite orientations from each other around the cavity. In use, the head region 202 of the cap remover 198 engages or grasps the top cap 42, and pivots about a point near the tail region 204 for opening the top cap, as designated by an arrow E (FIG. 17C). While a substantially round or oval shape of the cap remover 198 is shown in FIGS. 17A-17C for illustrative purposes, other suitable shapes or designs, such as multilateral or irregular shapes, are contemplated to suit the application.

Figure 17D:
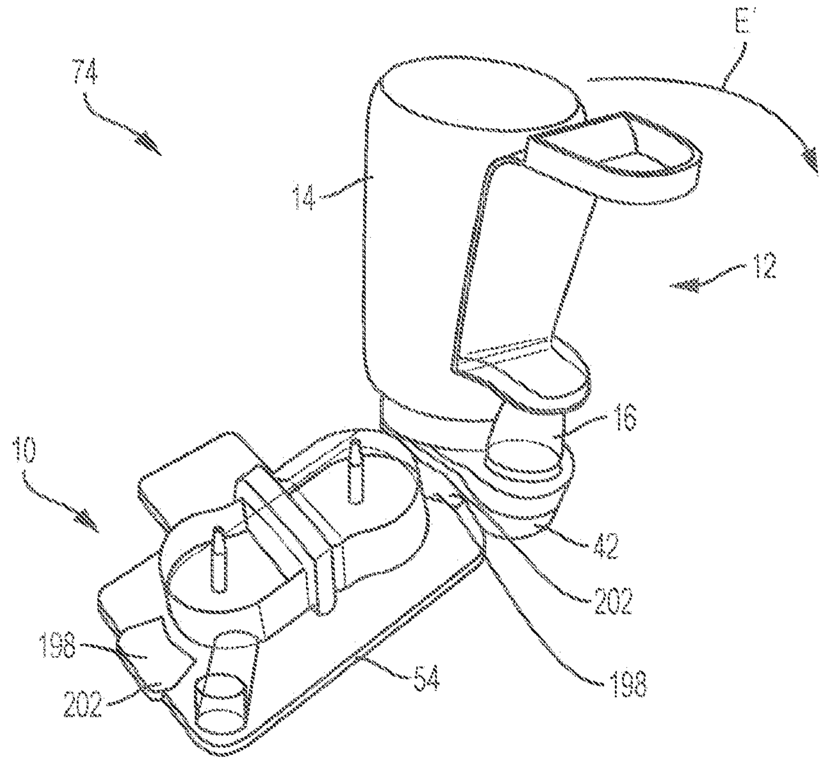

As shown in FIG. 17D, it is also contemplated that the head region 202 of the cap remover 198 is preferably integrally formed with the base 54 of the pooling device 10. In this configuration, the head region 202 of the cap remover 198 is fixedly attached to the base 54 of the pooling device 10 without the tail region 204. During use, the top cap 42 of the medical container unit 12 is positioned in an inverted position next to the pooling device 10 so that the head region 202 at the base 54 can engage or fit snuggly with the top cap of the container. Next, the container 14 pivots about a point opposite the head region 202 relative to the top cap 42, such that the container is pulled away from the pooling device 10 for opening the top cap, as designated by an arrow E'.

Figure 18:
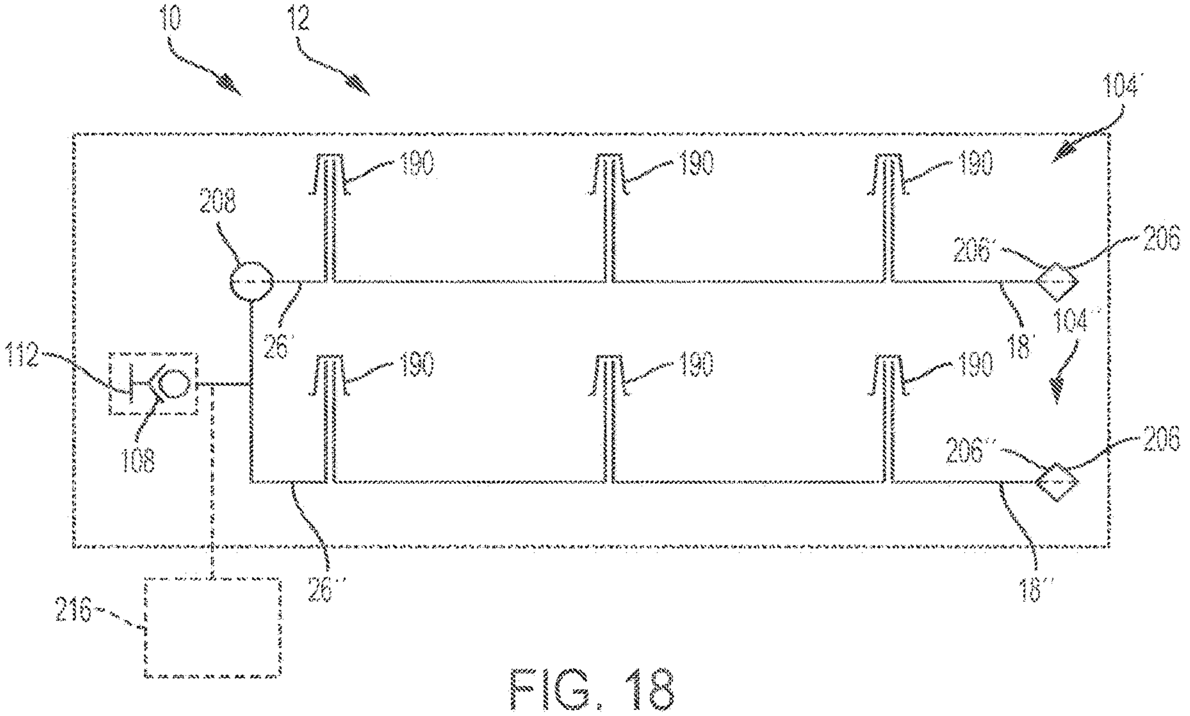
FIG. 18 is a schematic front view of the leakage prevention mechanism of FIG. 10, featuring an exemplary combination of a hydrophobic filter and a hydrophilic filter.

Referring now to FIGS. 1, 10, and 18, it is contemplated that in some embodiments the fluid connection assembly 104 includes at least one of a hydrophobic filter 206 and a hydrophilic filter 208. In some embodiments, the hydrophobic filter 206 is connected to the inlet port 18 of the pooling device 10 for selectively regulating a directional air/fluid flow of the pooling device. Conversely, the hydrophilic filter 208 is connected to the outlet port 26 of the pooling device 10 for selectively regulating the directional fluid and air flow of the pooling device.

In an exemplary configuration of FIG. 18, which is constructed and arranged for facilitating the dual medical container unit 12, a first hydrophobic filter 206' is connected to a first inlet port 18' for the first medical container 14 configured for storing the first medicinal fluid. Similarly, a second hydrophobic filter 206" is connected to a second inlet port 18" for the second medical container 16 configured for storing the second medicinal fluid. Thus, it is advantageous that the first and second hydrophobic filters 206', 206" allow air to vent without any unwanted fluid leakage from the inlet ports 18', 18".

To selectively control the directional fluid flow of the first or second medicinal fluid, the hydrophilic filter 208 is connected to both a first outlet port 26' for the first medical container 14, and a second outlet port 26" for the second medical container 16. In this configuration, the hydrophilic filter 208 advantageously allows air to vent until it becomes wet by the first or second medicinal fluid, after which the hydrophilic filter allows only the medicinal fluid to travel through the fluid path connector 112.

As an example only, when the first medical container 14 is empty of fluid, the hydrophilic filter 208 prevents air from passing the hydrophilic filter and being infused into a patient. This blocking of air also stops any fluid flow and causes the pump to sound an alarm, which signals the patient/caregiver to move the positional valve 216 to open the flow path to second medical container 16. Next, the pump operation is resumed to infuse the contents of second medical container 16. If the hydrophilic filter 208 is also installed in the outlet port 216", then the hydrophilic filter prevents air from passing the filter and being infused into the patient when the medical container 16 is empty. This blocking of air stops any fluid flow and causes the pump to sound an alarm, which signals the patient/caregiver that the infusion of the second medical fluid is complete. Other suitable arrangements of the hydrophobic and hydrophilic filters 206, 208 are also contemplated to suit different applications.

Figure 19:
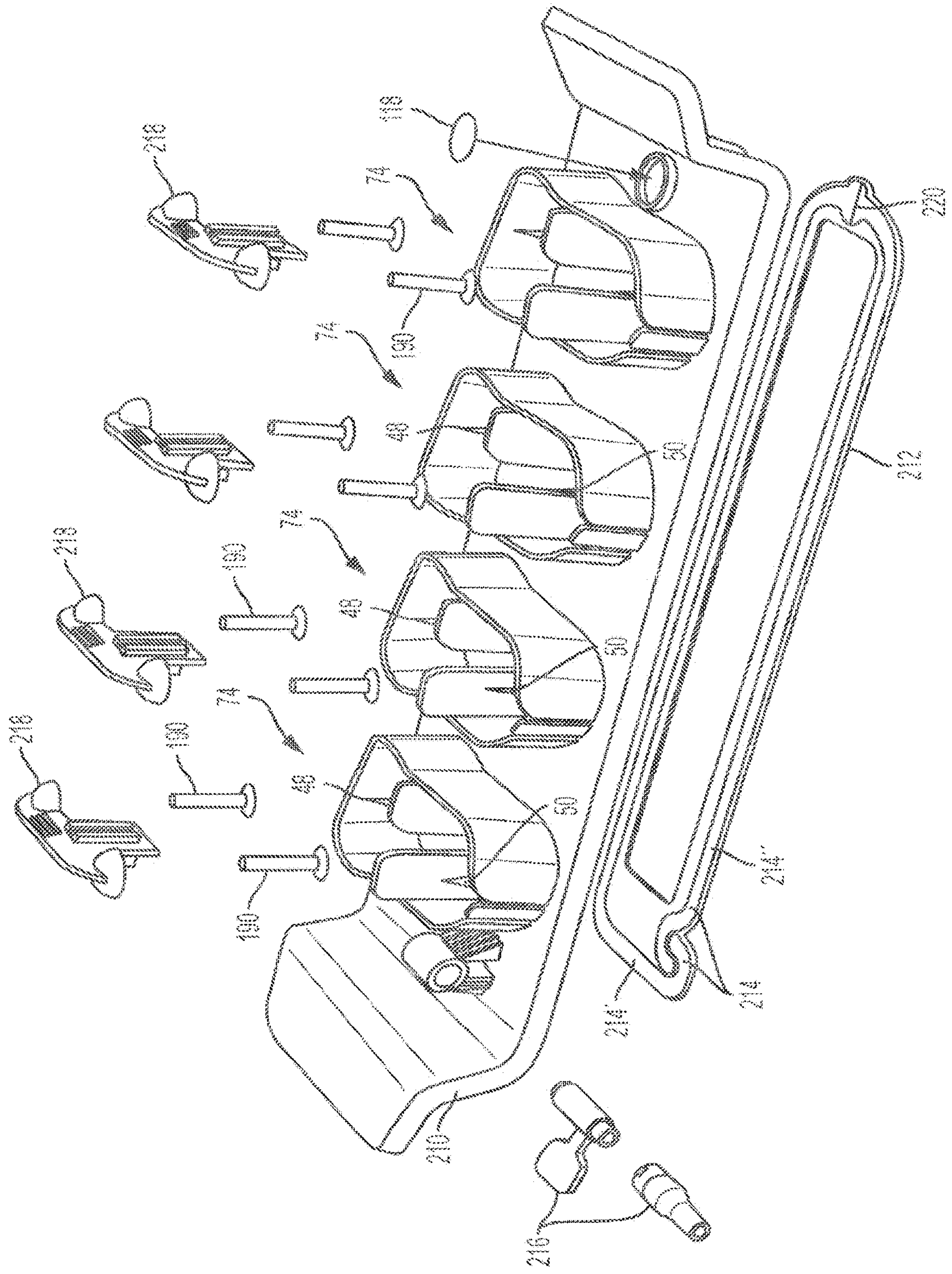
FIG. 19 is an exploded perspective view of an exemplary tray incorporating the present pooling device in a serial arrangement.

Referring now to FIGS. 1, 6, 7, 10, 11 and 19, it is contemplated that a tray member 210 includes at least one present pooling device 74 linked in a serial arrangement, incorporating the pooling device into the tray member in fluid communication. In FIG. 19, while four (4) pooling devices 74 are incorporated into the tray member 210, any number or embodiment of the pooling devices are contemplated to suit the application. A flow cover 212 having at least one flow path or passageway 214 is attached to the tray member 210 to facilitate the fluid communication between the pooling devices 74. It is preferred that a first flow passageway 214' is provided for connecting the first medical containers 14, and a separate second flow passageway 214" is provided for connecting the second medical containers 16. In this example, the tray member 210 includes a plurality of pooling devices 74 incorporated into the tray member in fluid communication. Further, the tray member 210 includes two separate tubes or passageway 214', 214" configured for conveying two separate fluids from the first and second medical containers 14, 16 to the outlet port 52. Components shared with the pooling device 10 shown in FIGS. 1, 6 and 11 are designated with identical reference numbers.

It is preferred that the tray member 210 includes a positional valve 216 configured for selectively allowing or regulating the fluid path from at least one of the first and second medical containers 14, 16. For example, the positional valve 216 is a manual switch or stopcock having a twist valve configured for selectively allowing and blocking the fluid flow from the first and/or second medical containers 14, 16. It is also contemplated that the positional valve 216 provides a valved access for preventing the fluid flow when the tubing set 28 is detached from the tray member 210. In a preferred embodiment, a spike cap 218 is provided to protect the spike sheath 190 and the spikes 48, 50. As an example, in FIG. 19, the fluid path connector 112 is replaced with the positional valve 216 for one path to the other at point 108. It is contemplated that the positional valve 216 has a luer lock connector and is axially rotatable so that the user controls which fluid is delivered to the user.

Referring now to FIGS. 1, 4, 7-9 and 20, it is preferred that the pooling device 74, 86*a* is constructed and arranged as a stackable, linkable modular unit. Components shared with the pooling devices 10, 74, 86*a* are designated with identical reference numbers. As similarly shown in FIGS. 4 and 7-9, it is contemplated that the pooling device 86*a* includes the first wing 88*a* configured for accommodating the outlet port 26*a*, and the second wing 90*a* configured for accommodating the inlet port 18*a*.

Figure 20:
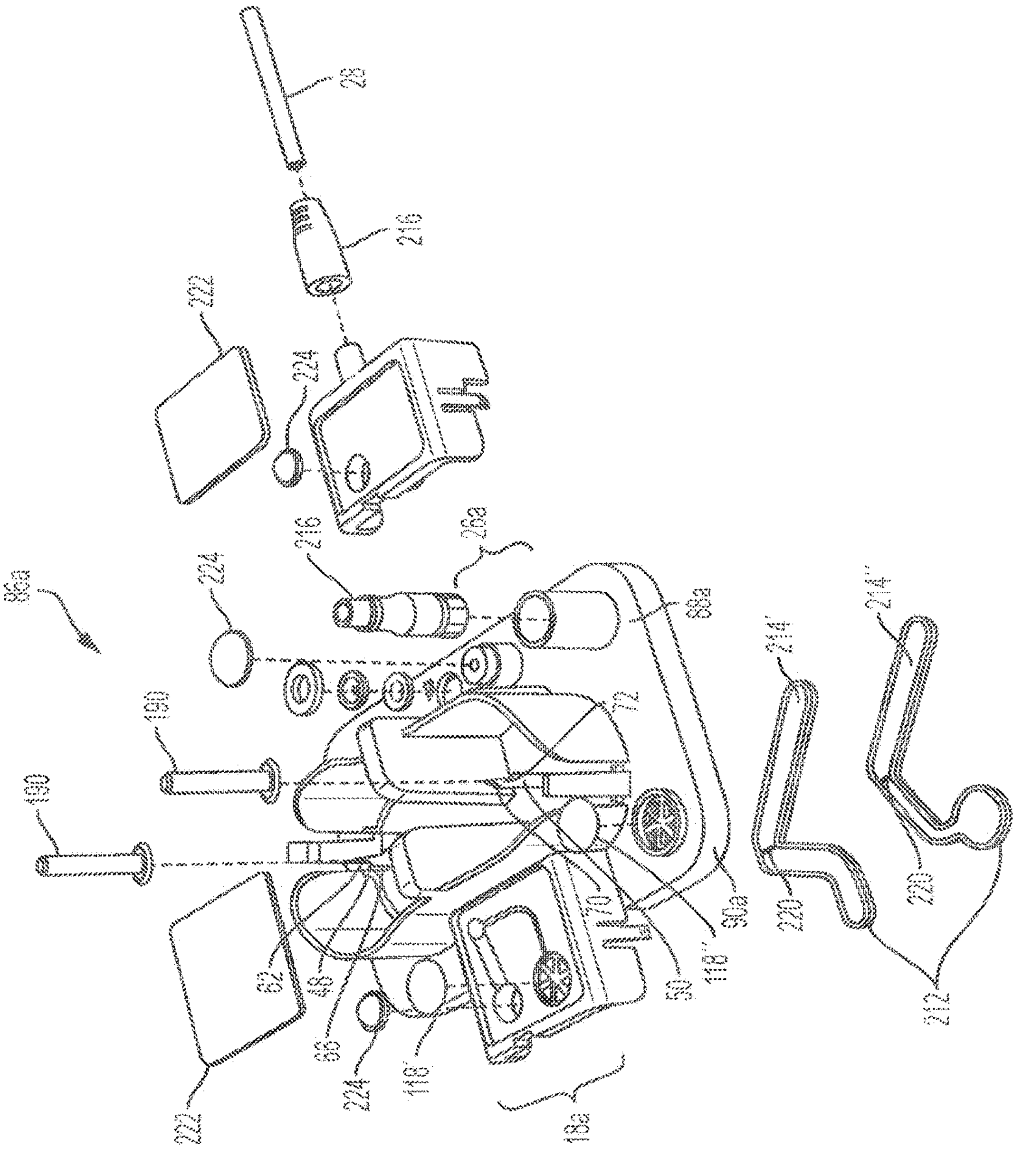
FIG. 20 is an exploded perspective view of an exemplary modular unit featuring the present pooling device with the hydrophobic filter.

To prevent unwanted leakage of the first and second medicinal fluids, as shown in FIG. 20, for example, a first hydrophobic filter 118' is disposed at the inlet port 18*a* and connected to the first spike 48, and a second hydrophobic filter 118" is disposed at the second wing 90*a* and connected to the second spike 50. Other suitable arrangements of the hydrophobic filters 118', 118" are contemplated to suit different applications.

As shown in FIG. 20, it is contemplated that the pooling device 86*a* includes the flow cover 212 having at least one dedicated flow path or passageway 214', 214" for facilitating the fluid flow from the respective spike 48, 50. Each flow path 214', 214" is bifurcated or separated according to the spike channels 62, 66, 70, 72 of the corresponding spike 48, 50 using a dividing member 220. It is also contemplated that at least one protective plate or cover 222 is provided to seal exposed fluid or air paths or passageways associated with the pooling device 86*a*. Further, at least one cap member 224 is provided to detachably block the fluid or air path or passageway associated with the pooling device 86*a*.

While a particular embodiment of the present pooling device has been described herein, it will be appreciated by those skilled in the art that changes and modifications may be made thereto without departing from the present disclosure in its broader aspects, and as set forth in the following claims.

What is claimed is:

1. A pooling device for pooling a medicinal fluid, comprising:

one or more inlets configured for receiving ambient air;

one or more outlets configured for delivering the medicinal fluid to an attachment;

a first cavity configured for accommodating insertion of a first container unit having a first container configured to store a first fluid and a second container configured to store a second fluid, a first spike disposed in the first cavity and configured for puncturing a stopper of the first container when the first container unit transitions from an upper position to a lower position;

a second spike disposed in the first cavity and configured for puncturing a stopper of the second container when the first container unit transitions from an upper position to a lower position;

a first flow passageway connected to the first spike and configured to convey the first fluid from the first container to a first outlet of the one or more outlets; and a second flow passageway separate from the first flow passageway such that fluid communication between the second flow passageway and the first flow passageway is closed, wherein the second flow passageway is connected to the second spike and configured to convey the second fluid from the second container to a second outlet of the one or more outlets, wherein the second flow passageway is configured to convey the second fluid to the second outlet without receiving fluid from the first flow passageway, and wherein the first flow passageway is configured to convey the first fluid to the first outlet without receiving fluid from the second flow passageway.

2. The pooling device of claim 1, wherein the first cavity is dimensioned such that the first container unit can only be inserted into the first cavity in a single orientation.

3. The pooling device of claim 1, further comprising:

a second cavity configured for accommodating insertion of a second container unit having a third container configured to store a third fluid and a fourth container configured to store a fourth fluid, a third spike disposed in the second cavity and configured for puncturing a stopper of the third container when the second container unit transitions from an upper position to a lower position, wherein the third spike is connected to the first flow passageway and the first flow passageway is further configured to convey the third fluid from the third container to the first outlet; and a fourth spike disposed in the second cavity and configured for puncturing a stopper of the fourth container when the second container unit transitions from an upper position to a lower position, wherein the fourth spike is connected to the second flow passageway and the second flow passageway is further configured to convey the fourth fluid from the fourth container to the second outlet.

4. The pooling device of claim 3, further comprising the first container unit and the second container unit, wherein the first fluid and the third fluid are both a first type fluid, and wherein the second fluid and the fourth fluid are both a second type fluid, and wherein the first type fluid and the second type fluid are different fluid types.

5. The pooling device of claim 3, wherein the second cavity is dimensioned such that the second container unit can only be inserted into the second cavity in a single orientation.

6. The pooling device of claim 3, wherein the first cavity and the second cavity are integrated into a tray member.

7. The pooling device of claim 3, further comprising:

a third cavity configured for accommodating insertion of a third container unit having a fifth container configured to store a fifth fluid and a sixth container configured to store a sixth fluid, a fifth spike disposed in the third cavity and configured for puncturing a stopper of the fifth container when the third container unit transitions from an upper position to a lower position, wherein the fifth spike is connected to the first flow passageway and the first flow passageway is further configured to convey the fifth fluid from the fifth container to the first outlet; and a sixth spike disposed in the third cavity and configured for puncturing a stopper of the sixth container when the third container unit transitions from an upper position to a lower position, wherein the sixth spike is connected to the second flow passageway and the second flow passageway is further configured to convey the sixth fluid from the sixth container to the second outlet.

8. The pooling device of claim 7, further comprising:

a fourth cavity configured for accommodating insertion of a fourth container unit having a seventh container configured to store a seventh fluid and an eighth container configured to store an eighth fluid, a seventh spike disposed in the fourth cavity and configured for puncturing a stopper of the seventh container when the fourth container unit transitions from an upper position to a lower position, wherein the seventh spike is connected to the first flow passageway and the first flow passageway is further configured to convey the seventh fluid from the seventh container to the first outlet; and an eighth spike disposed in the fourth cavity and configured for puncturing a stopper of the eighth container when the fourth container unit transitions from an upper position to a lower position, wherein the eighth spike is connected to the second flow passageway and the second flow passageway is further configured to convey the eighth fluid from the eighth container to the second outlet.

9. The pooling device of claim 1, wherein the first spike includes a first channel connected to the one or more inlets and a second channel connected to the first outlet.

10. The pooling device of claim 9, further comprising a spike sheath connecting the first channel and the second channel in fluid communication when the spike sheath is unpunctured.

11. The pooling device of claim 10, wherein the spike sheath is configured to be punctured and compressed when the first container unit transitions from the upper position to the lower position.

12. The pooling device of claim 1, further comprising a locking mechanism configured for securely holding the first container unit in the first cavity during use.

13. The pooling device of claim 12, wherein the locking mechanism is disposed on an inner wall of the first cavity.

14. A method of operating a pooling device for pooling a medicinal fluid, the method comprising:

inserting a first container unit including a first container containing a first fluid and a second container containing a second fluid into a first cavity;

moving the first container unit from an upper position to a lower position in the first cavity;

piercing a stopper of the first container with a first spike disposed in the first cavity;

allowing the first fluid to flow from the first container into the first spike, through a first flow passageway, and to a first outlet of the pooling device;

piercing a stopper of the second container with a second spike disposed in the first cavity; and allowing the second fluid to flow from the second container into the second spike, through a second flow passageway, and to a second outlet of the pooling device, wherein fluid communication between the second flow passageway and the first flow passageway is closed, wherein the second flow passageway is configured to convey the second fluid to the second outlet without receiving fluid from the first flow passageway, and wherein the first flow passageway is configured to convey the first fluid to the first outlet without receiving fluid from the second flow passageway.

15. The method of claim 14, wherein the first cavity is dimensioned such that the first container unit can only be inserted into the first cavity in a single orientation.

16. The method of claim 14, further comprising:

inserting a second container unit including a third container containing a third fluid and a fourth container containing a fourth fluid into a second cavity;

moving the second container unit from an upper position to a lower position in the second cavity;

piercing a stopper of the third container with a third spike disposed in the second cavity;

allowing the third fluid to flow from the third container into the third spike, through the first flow passageway, and to the first outlet;

piercing a stopper of the fourth container with a fourth spike disposed in the second cavity; and allowing the fourth fluid to flow from the fourth container into the fourth spike, through the second flow passageway, and to the second outlet.

17. The method of claim 16, wherein the first fluid and the third fluid are both a first type fluid, and wherein the second fluid and the fourth fluid are both a second type fluid, and wherein the first type fluid and the second type fluid are different fluid types.

18. The method of claim 16, wherein the second cavity is dimensioned such that the second container unit can only be inserted into the second cavity in a single orientation.

19. The method of claim 16, wherein the first cavity and the second cavity are integrated into a tray member.

20. The method of claim 14, further comprising holding the first container in the first cavity with a locking mechanism disposed on an inner wall of the first cavity.

* * * * *